US 11,576,964 B2

United States Patent
Strugnell et al.

(10) Patent No.: US 11,576,964 B2
(45) Date of Patent: Feb. 14, 2023

(54) METHODS OF GENERATING BROADLY PROTECTIVE VACCINE COMPOSITIONS COMPRISING HEMAGGLUTININ

(71) Applicant: SANOFI PASTEUR INC., Swiftwater, PA (US)

(72) Inventors: Tod Strugnell, Carlisle, MA (US); Eliud Oloo, Arlington, MA (US); Raymond Oomen, Cambridge, MA (US); Thorsten Vogel, Cambridge, MA (US); Harold Kleanthous, Chelmsford, MA (US)

(73) Assignee: Sanofi Pasteur Inc., Cambridge, MA (US)

( * ) Notice: Subject to any disclaimer, the term of this patent is extended or adjusted under 35 U.S.C. 154(b) by 42 days.

(21) Appl. No.: 17/041,784

(22) PCT Filed: Mar. 27, 2019

(86) PCT No.: PCT/US2019/024323
§ 371 (c)(1),
(2) Date: Sep. 25, 2020

(87) PCT Pub. No.: WO2019/191257
PCT Pub. Date: Oct. 3, 2019

(65) Prior Publication Data
US 2021/0128715 A1 May 6, 2021

Related U.S. Application Data

(60) Provisional application No. 62/649,004, filed on Mar. 28, 2018.

(51) Int. Cl.
| | | |
|---|---|---|
| *A61K 39/145* | (2006.01) | |
| *C07K 14/11* | (2006.01) | |
| *A61P 31/16* | (2006.01) | |
| *A61K 38/00* | (2006.01) | |
| *A61K 39/00* | (2006.01) | |

(52) U.S. Cl.
CPC ........... *A61K 39/145* (2013.01); *A61P 31/16* (2018.01); *C07K 14/11* (2013.01); *A61K 38/00* (2013.01); *A61K 2039/5258* (2013.01)

(58) Field of Classification Search
None
See application file for complete search history.

(56) References Cited

FOREIGN PATENT DOCUMENTS

| EP | 2831094 B1 | 6/2018 |
|---|---|---|
| WO | 2010036970 A2 | 4/2010 |
| WO | 2012036993 A1 | 3/2012 |
| WO | 2013148164 A1 | 10/2013 |
| WO | 2016196846 A2 | 12/2016 |

OTHER PUBLICATIONS

Carter et al. (Journal of Virology, 2016, p. 4720-4734) in IDS on Mar. 26, 2021.*
Giles et al. (Vaccine, 2011, p. 3042-3054) in IDS on Mar. 26, 2021.*
Carter et al., "Design and Characterization of a Computationally Optimized Broadly Reactive Hemagglutinin Vaccine for H1N1 Influenza Viruses", Journal of Virology, 90(9), pp. 4720-4734 (Feb. 24, 2016).
Giles et al., "A computationally optimized broadly reactive antigen (COBRA) based H5N1 VLP vaccine elicits broadly Yeactive antibodies in mice and ferrets", Vaccine, 29(16), pp. 3043-3054 (Apr. 1, 2011).
Notification of Transmittal of the International Search Report and the Written Opinion of the International Searching Authority, or the Declaration, issued in International Application No. PCT/US2019/024323, dated Jul. 31, 2019 (22 pages).
Pessia et al., "K-Pax2: Bayesian identification of cluster-defining amino acid positions in large sequence datasets", Microbial Genomics, 1(1) (Jul. 15, 2015) (1 page).

* cited by examiner

*Primary Examiner* — Agnieszka Boesen
(74) *Attorney, Agent, or Firm* — McNeill Baur PLLC

(57) ABSTRACT

The present disclosure relates to a cluster-based consensus approach for generating recombinant hemagglutinin (HA) polypeptides. The disclosure further relates to influenza vaccine compositions comprising the recombinant HA polypeptides.

9 Claims, 21 Drawing Sheets

Specification includes a Sequence Listing.

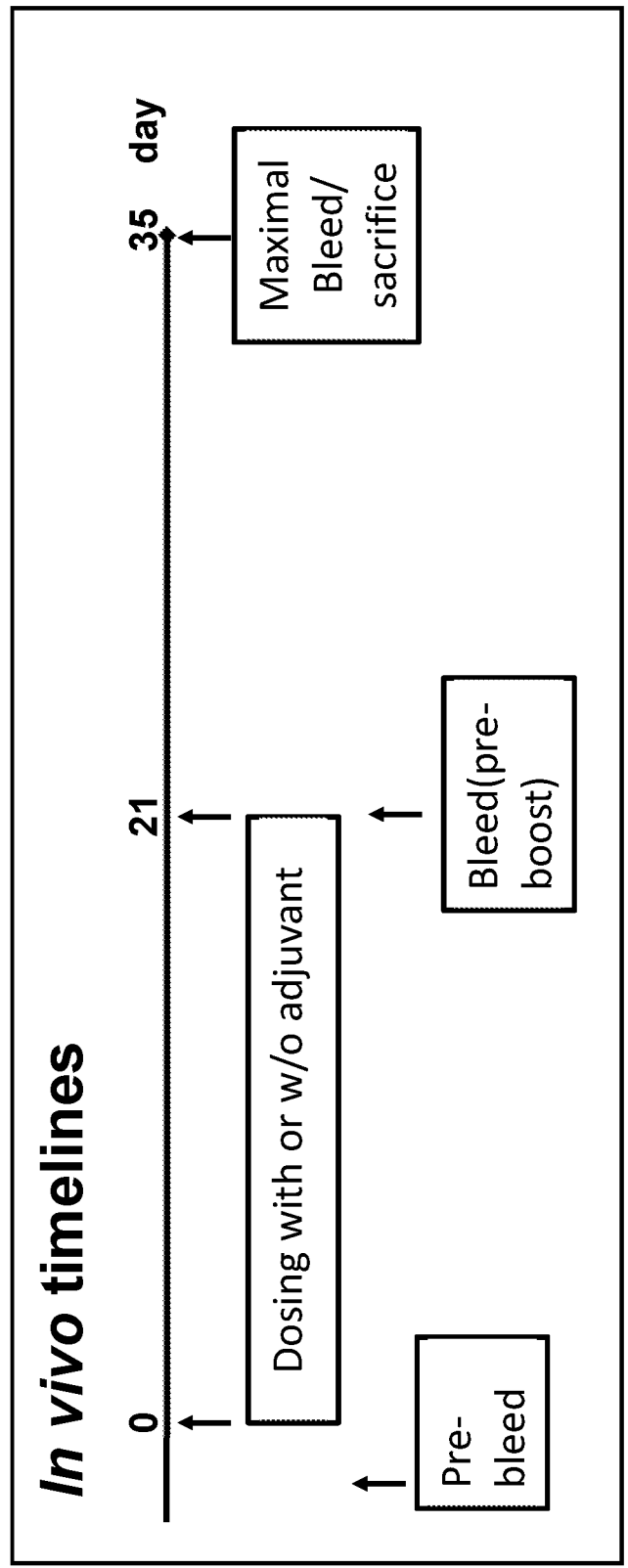

SEQUENCE LISTING

<160> NUMBER OF SEQ ID NOS: 33

<210> SEQ ID NO 1
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

```
Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
            165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Thr Ser Arg Tyr Ser
            210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
            245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
            325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
            405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
            500                 505                 510
```

```
Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 2
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Arg His Asn Gly Lys Leu Cys Lys Leu Arg Gly Val
            50                  55                  60

Ala Pro Leu His Leu Gly Lys Cys Asn Ile Ala Gly Trp Leu Leu Gly
65                  70                  75                  80

Asn Pro Glu Cys Glu Leu Leu Phe Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
            115                 120                 125

Glu Arg Phe Glu Ile Phe Pro Lys Ala Ser Ser Trp Pro Asn His Glu
130                 135                 140

Thr Asn Arg Gly Val Thr Ala Ala Cys Pro Tyr Ala Gly Ala Asn Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Val Asn Asn Lys Gly Lys Glu Val Leu Val
            180                 185                 190

Leu Trp Gly Ile His His Pro Pro Thr Ser Thr Asp Gln Gln Ser Leu
            195                 200                 205

Tyr Gln Asn Ala Asp Ala Tyr Val Phe Val Gly Ser Ser Lys Tyr Asn
            210                 215                 220

Lys Lys Phe Lys Pro Glu Ile Ala Thr Arg Pro Lys Val Arg Gly Gln
225                 230                 235                 240

Ala Gly Arg Met Asn Tyr Tyr Trp Thr Leu Ile Glu Pro Gly Asp Thr
                245                 250                 255

Ile Thr Phe Glu Ala Thr Gly Asn Leu Val Val Pro Arg Tyr Ala Phe
            260                 265                 270

Ala Met Lys Arg Gly Ser Gly Ser Gly Ile Ile Ile Ser Asp Ala Pro
            275                 280                 285

Val His Asp Cys Asn Thr Thr Cys Gln Thr Pro Lys Gly Ala Ile Asn
```

```
                290                 295                 300
Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
                450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
                515                 520                 525

Gln Ile Leu Ala Ile Tyr Ser Thr Val Ala Ser Ser Leu Val Leu Leu
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 3
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asn Ser His Asn Gly Lys Leu Cys Leu Leu Lys Gly Ile
                50                  55                  60

Ala Pro Leu Gln Leu Gly Asn Cys Ser Val Ala Gly Trp Ile Leu Gly
65                  70                  75                  80
```

```
Asn Pro Glu Cys Glu Leu Leu Ile Ser Lys Glu Ser Trp Ser Tyr Ile
                85                  90                  95
Val Glu Lys Pro Asn Pro Glu Asn Gly Thr Cys Tyr Pro Gly His Phe
            100                 105                 110
Ala Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Thr
    130                 135                 140
Val Thr Gly Val Ser Ala Ser Cys Ser His Asn Gly Glu Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
            180                 185                 190
Trp Gly Val His His Pro Pro Asn Ile Gly Asp Gln Lys Thr Leu Tyr
        195                 200                 205
His Thr Glu Asn Ala Tyr Val Ser Val Val Ser Ser His Tyr Ser Arg
    210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Asn Ser Asn Ala Pro Met
        275                 280                 285
Asp Lys Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
```

```
Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 4
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
```

Asp Glu Cys Asp Ala Lys Cys Gln Thr Pro Gln Gly Ala Ile Asn Ser
            275                 280                 285
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Gln Lys Ser Thr
                370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
                435                 440                 445

Arg Thr Leu Asp Phe His Asp Ser Asn Val Lys Asn Leu Tyr Glu Lys
                450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Arg Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 5
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Lys Val Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Thr
        50                  55                  60

```
Ala Pro Leu Gln Leu Gly Asn Cys Ser Val Ala Gly Trp Ile Leu Gly
 65                  70                  75                  80

Asn Pro Glu Cys Glu Ser Leu Phe Ser Lys Glu Ser Trp Ser Tyr Ile
                 85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Gly Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Lys Asn Asn Ala Lys Glu Ile Gly Asn Gly
465                 470                 475                 480
```

```
Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 6
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Lys Arg Pro Lys Val Arg Gly Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
```

Ala Leu Ser Arg Gly Phe Gly Ser Gly Ile Ile Thr Ser Asn Ala Ser
                275                 280                 285

Met Asp Glu Cys Asp Ala Lys Cys Gln Thr Pro Gln Gly Ala Ile Asn
        290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 7
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

```
Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
 65                  70                  75                  80

Asn Pro Glu Cys Glu Ser Leu Leu Ser Asn Arg Ser Trp Ser Tyr Ile
                 85                  90                  95

Ala Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Thr Thr Arg Gly Val Thr Ala Ala Cys Ser His Ala Lys Lys Ser Ser
145                 150                 155                 160

Phe Tyr Lys Asn Leu Leu Trp Leu Thr Glu Lys Asn Gly Ser Tyr Pro
                165                 170                 175

Asn Leu Ser Arg Ser Tyr Val Asn Asn Lys Glu Lys Glu Val Leu Val
            180                 185                 190

Leu Trp Gly Val His His Pro Ser Asn Ile Glu Asp Gln Arg Thr Leu
    195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Leu Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Met Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460
```

```
Lys Val Lys Asn Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Lys Asn Gly Thr Tyr Asp Tyr Pro Lys Tyr Ser Glu Ser Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
            565
```

<210> SEQ ID NO 8
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Asn Gly Val Thr Ala Ala Cys Ser His Glu Gly Lys Ser Ser
145                 150                 155                 160

Phe Tyr Arg Asn Leu Leu Trp Leu Thr Lys Lys Gly Ser Tyr Pro
                165                 170                 175

Lys Leu Lys Asn Ser Tyr Val Asn Lys Lys Gly Lys Glu Val Leu Val
            180                 185                 190

Leu Trp Gly Val His His Pro Ser Asn Ser Lys Glu Gln Gln Asn Leu
        195                 200                 205

Tyr Gln Asn Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
```

```
                  245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
                275                 280                 285

Met His Glu Cys Asn Thr Lys Cys Gln Thr Pro Leu Gly Ala Ile Asn
            290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Phe His Asp Ser Asn Val Lys Asn Leu Tyr Glu
            450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 9
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30
```

```
Val Asp Thr Val Leu Glu Lys Asn Val Thr Val Thr His Ser Val Asn
     35                  40                  45

Leu Leu Glu Asp Lys His Asn Gly Lys Leu Cys Lys Leu Arg Gly Val
 50                  55                  60

Ala Pro Leu His Leu Gly Lys Cys Asn Ile Ala Gly Trp Ile Leu Gly
 65                  70                  75                  80

Asn Pro Glu Cys Glu Ser Leu Phe Thr Ala Ser Ser Trp Ser Tyr Ile
                 85                  90                  95

Val Glu Thr Ser Asn Ser Asp Asn Gly Thr Cys Tyr Pro Gly Asp Phe
                100                 105                 110

Ile Asn Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
    130                 135                 140

Thr Asn Arg Gly Val Thr Ala Ala Cys Pro His Ala Gly Ala Lys Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
    195                 200                 205

Tyr Gln Asn Ala Asp Ala Tyr Val Phe Val Gly Ser Ser Lys Tyr Ser
210                 215                 220

Lys Lys Phe Lys Pro Glu Ile Ala Thr Arg Pro Lys Val Arg Asp Gln
225                 230                 235                 240

Ala Gly Arg Met Asn Tyr Tyr Trp Thr Leu Val Glu Pro Gly Asp Thr
                245                 250                 255

Ile Thr Phe Glu Ala Thr Gly Asn Leu Val Val Pro Arg Tyr Ala Phe
            260                 265                 270

Ala Met Lys Arg Gly Ser Gly Ser Gly Ile Ile Ile Ser Asp Thr Pro
    275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
    355                 360                 365

His His Gln Asn Glu Gln Gly Ser Gly Tyr Ala Ala Asp Gln Lys Ser
370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
    435                 440                 445
```

```
Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Val
                530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 10
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Arg Ser Trp Pro Lys His Asn
    130                 135                 140

Ile Thr Arg Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
                180                 185                 190

Leu Trp Gly Val His His Pro Ser Asn Ile Glu Asp Gln Lys Thr Leu
            195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Lys Arg Pro Lys Val Arg Gly Gln
```

-continued

```
            225                 230                 235                 240
        Glu Gly Arg Ile Asn Tyr Tyr Trp Thr Leu Leu Glu Pro Gly Asp Thr
                        245                 250                 255
        Ile Ile Phe Glu Ala Asn Gly Asn Leu Ile Ala Pro Trp Tyr Ala Phe
                        260                 265                 270
        Ala Leu Ser Arg Gly Phe Gly Ser Gly Ile Ile Thr Ser Asn Ala Ser
                        275                 280                 285
        Met Asp Glu Cys Asp Thr Lys Cys Gln Thr Pro Gln Gly Ala Ile Asn
                290                 295                 300
        Ser Ser Leu Pro Phe Gln Asn Val His Pro Val Thr Ile Gly Glu Cys
        305                 310                 315                 320
        Pro Lys Tyr Val Arg Ser Thr Lys Leu Arg Met Val Thr Gly Leu Arg
                        325                 330                 335
        Asn Ile Pro Ser Ile Gln Ser Arg Gly Leu Phe Gly Ala Ile Ala Gly
                        340                 345                 350
        Phe Ile Glu Gly Gly Trp Thr Gly Met Ile Asp Gly Trp Tyr Gly Tyr
                        355                 360                 365
        His His Gln Asn Glu Gln Gly Ser Gly Tyr Ala Ala Asp Gln Lys Ser
                370                 375                 380
        Thr Gln Asn Ala Ile Asn Gly Ile Thr Asn Lys Val Asn Ser Val Ile
        385                 390                 395                 400
        Glu Lys Met Asn Thr Gln Phe Thr Ala Val Gly Lys Glu Phe Asn Lys
                        405                 410                 415
        Leu Glu Lys Arg Met Glu Asn Leu Asn Lys Lys Val Asp Asp Gly Phe
                        420                 425                 430
        Leu Asp Ile Trp Thr Tyr Asn Ala Glu Leu Leu Val Leu Leu Glu Asn
                        435                 440                 445
        Glu Arg Thr Leu Asp Phe His Asp Ser Asn Val Lys Asn Leu Tyr Glu
                450                 455                 460
        Lys Val Lys Asn Gln Leu Lys Asn Asn Ala Lys Glu Ile Gly Asn Gly
        465                 470                 475                 480
        Cys Phe Glu Phe Tyr His Lys Cys Asn Asn Glu Cys Met Glu Ser Val
                        485                 490                 495
        Lys Asn Gly Thr Tyr Asp Tyr Pro Lys Tyr Ser Glu Glu Ser Lys Leu
                        500                 505                 510
        Asn Arg Glu Lys Ile Asp Gly Val Lys Leu Glu Ser Met Gly Val Tyr
                        515                 520                 525
        Gln Ile Leu Ala Ile Tyr Ser Thr Val Ala Ser Ser Leu Val Leu Leu
                530                 535                 540
        Val Ser Leu Gly Ala Ile Ser Phe Trp Met Cys Ser Asn Gly Ser Leu
        545                 550                 555                 560
        Gln Cys Arg Ile Cys Ile
                        565

<210> SEQ ID NO 11
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Lys Val Lys Leu Leu Val Leu Leu Cys Thr Phe Thr Ala Thr Tyr
1               5                   10                  15
```

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Thr Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
            210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Thr Ser Asn Ala Pro Met
            275                 280                 285

Asp Glu Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430
```

Asp Ile Trp Thr Tyr Asn Ala Glu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 12
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Val Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Arg Gly Val Thr Ala Ala Cys Ser His Asn Gly Lys Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Gln Thr Leu
        195                 200                 205

Tyr Gln Asn Glu Asn Ala Tyr Val Ser Val Val Ser Ser Asn Tyr Ser

```
            210                 215                 220
Arg Arg Phe Thr Pro Glu Ile Ala Lys Arg Pro Lys Val Arg Asp Gln
225                 230                 235                 240

Glu Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 13
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
50                  55                  60

Ala Pro Leu Gln Leu Gly Lys Cys Asn Ile Ala Gly Trp Ile Leu Gly
65                      70                  75                  80

Asn Pro Glu Cys Glu Ser Leu Phe Ser Lys Glu Ser Trp Ser Tyr Ile
                85                  90                  95

Val Glu Thr Pro Asn Ser Glu Asn Gly Thr Cys Tyr Pro Gly Asp Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Thr Arg Gly Val Thr Ala Ala Cys Ser His Asn Gly Lys Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
                180                 185                 190

Leu Trp Gly Val His His Pro Ser Asn Ile Gly Asp Gln Gln Thr Leu
            195                 200                 205

Tyr Gln Asn Glu Asn Ala Tyr Val Ser Val Val Ser Ser Asn Tyr Ser
210                 215                 220

Arg Arg Phe Thr Pro Glu Ile Ala Lys Arg Pro Lys Val Arg Asp Gln
225                 230                 235                 240

Glu Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Pro
            275                 280                 285

Met Asp Glu Cys Asp Thr Lys Cys Gln Thr Pro Gln Gly Ala Ile Asn
            290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415
```

```
Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Met Gly Val Tyr
    515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 14
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Glu Ser Trp Ser Tyr Ile
            85                  90                  95

Val Glu Thr Pro Asn Ser Glu Asn Gly Thr Cys Tyr Pro Gly Asp Phe
        100                 105                 110

Ala Asp Tyr Glu Glu Leu Arg Glu Gln Leu Ser Ser Val Ser Ser Phe
    115                 120                 125

Glu Arg Phe Glu Ile Phe Pro Lys Glu Ser Ser Trp Pro Asn His Asn
130                 135                 140

Thr Thr Arg Gly Val Thr Ala Ala Cys Ser His Asn Gly Lys Ser Ser
145                 150                 155                 160

Phe Tyr Arg Asn Leu Leu Trp Leu Thr Lys Lys Asn Gly Ser Tyr Pro
            165                 170                 175

Asn Leu Ser Lys Ser Tyr Val Asn Asn Lys Glu Lys Glu Val Leu Val
        180                 185                 190

Leu Trp Gly Val His His Pro Ser Asn Ile Gly Asp Gln Gln Thr Leu
```

```
                    195                 200                 205
Tyr Gln Asn Glu Asn Ala Tyr Val Ser Val Ser Ser Asn Tyr Ser
210                 215                 220
Arg Arg Phe Thr Pro Glu Ile Ala Lys Arg Pro Lys Val Arg Asp Gln
225                 230                 235                 240
Glu Gly Arg Met Asn Tyr Tyr Trp Thr Leu Glu Pro Gly Asp Thr
                245                 250                 255
Ile Ile Phe Glu Ala Asn Gly Asn Leu Ile Ala Pro Trp Tyr Ala Phe
                260                 265                 270
Ala Leu Ser Arg Gly Phe Gly Ser Gly Ile Ile Thr Ser Asn Ala Ser
                275                 280                 285
Met Asp Glu Cys Asp Thr Lys Cys Gln Thr Pro Gln Gly Ala Ile Asn
                290                 295                 300
Ser Ser Leu Pro Phe Gln Asn Ile His Pro Val Thr Ile Gly Glu Cys
305                 310                 315                 320
Pro Lys Tyr Val Arg Ser Thr Lys Leu Arg Met Val Thr Gly Leu Arg
                325                 330                 335
Asn Ile Pro Ser Ile Gln Ser Arg Gly Leu Phe Gly Ala Ile Ala Gly
                340                 345                 350
Phe Ile Glu Gly Gly Trp Thr Gly Met Ile Asp Gly Trp Tyr Gly Tyr
                355                 360                 365
His His Gln Asn Glu Gln Gly Ser Gly Tyr Ala Ala Asp Gln Lys Ser
                370                 375                 380
Thr Gln Asn Ala Ile Asn Gly Ile Thr Asn Lys Val Asn Ser Val Ile
385                 390                 395                 400
Glu Lys Met Asn Thr Gln Phe Thr Ala Val Gly Lys Glu Phe Asn Lys
                405                 410                 415
Leu Glu Lys Arg Met Glu Asn Leu Asn Lys Lys Val Asp Asp Gly Phe
                420                 425                 430
Leu Asp Ile Trp Thr Tyr Asn Ala Glu Leu Leu Val Leu Leu Glu Asn
                435                 440                 445
Glu Arg Thr Leu Asp Phe His Asp Ser Asn Val Lys Asn Leu Tyr Glu
                450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asp Asn Glu Cys Met Glu Ser Val
                485                 490                 495
Lys Asn Gly Thr Tyr Asp Tyr Pro Lys Tyr Ser Glu Glu Ala Lys Leu
                500                 505                 510
Asn Arg Glu Glu Ile Asp Gly Val Lys Leu Glu Ser Met Gly Val Tyr
                515                 520                 525
Gln Ile Leu Ala Ile Tyr Ser Thr Val Ala Ser Ser Leu Val Leu Leu
                530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 15
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 15

```
Met Lys Ala Lys Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Val Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
130                 135                 140

Val Thr Arg Gly Val Thr Ala Ala Cys Ser His Asn Gly Lys Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Gln Thr Leu
            195                 200                 205

Tyr Gln Asn Glu Asn Ala Tyr Val Ser Val Val Ser Ser Asn Tyr Ser
            210                 215                 220

Arg Arg Phe Thr Pro Glu Ile Ala Lys Arg Pro Lys Val Arg Asp Gln
225                 230                 235                 240

Glu Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Ser
            275                 280                 285

Met Asp Glu Cys Asp Thr Lys Cys Gln Thr Pro Gln Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400
```

-continued

```
Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 16
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Val Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Val Thr Arg Gly Val Thr Ala Ala Cys Ser His Asn Gly Lys Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
```

```
                180                 185                 190
Leu Trp Gly Val His His Pro Ser Asn Ile Gly Asp Gln Gln Thr Leu
            195                 200                 205
Tyr Gln Asn Glu Asn Ala Tyr Val Ser Val Ser Ser Asn Tyr Ser
    210                 215                 220
Arg Arg Phe Thr Pro Glu Ile Ala Lys Arg Pro Lys Val Arg Asp Gln
225                 230                 235                 240
Glu Gly Arg Met Asn Tyr Tyr Trp Thr Leu Leu Glu Pro Gly Asp Thr
                245                 250                 255
Ile Ile Phe Glu Ala Asn Gly Asn Leu Ile Ala Pro Trp Tyr Ala Phe
            260                 265                 270
Ala Leu Ser Arg Gly Phe Gly Ser Gly Ile Ile Thr Ser Asn Ala Ser
        275                 280                 285
Met Asp Glu Cys Asp Thr Lys Cys Gln Thr Pro Gln Gly Ala Ile Asn
    290                 295                 300
Ser Ser Leu Pro Phe Gln Asn Ile His Pro Val Thr Ile Gly Glu Cys
305                 310                 315                 320
Pro Lys Tyr Val Arg Ser Thr Lys Leu Arg Met Val Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Ile Asp Gly Trp Tyr Gly Tyr
        355                 360                 365
His His Gln Asn Glu Gln Gly Ser Gly Tyr Ala Ala Asp Gln Lys Ser
    370                 375                 380
Thr Gln Asn Ala Ile Asn Gly Ile Thr Asn Lys Val Asn Ser Val Ile
385                 390                 395                 400
Glu Lys Met Asn Thr Gln Phe Thr Ala Val Gly Lys Glu Phe Asn Lys
                405                 410                 415
Leu Glu Lys Arg Met Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Phe His Asp Ser Asn Val Lys Asn Leu Tyr Glu
    450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asp Asn Glu Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Met Gly Val Tyr
        515                 520                 525
Gln Ile Leu Ala Ile Tyr Ser Thr Val Ala Ser Ser Leu Val Leu Leu
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 17
<211> LENGTH: 23
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 17

Met Pro Met Gly Ser Leu Gln Pro Leu Ala Thr Leu Tyr Leu Leu Gly
1               5                   10                  15

Met Leu Val Ala Ser Val Leu
            20

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Trp Ser His Pro Gln Phe Glu Lys
1               5

<210> SEQ ID NO 19
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(40)
<223> OTHER INFORMATION: /note="This sequence may encompass 1-8 'Gly Gly
      Gly Gly Ser' repeating units"

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Gly Ser Gly Gly Ser Gly Gly Gly Gly Ser Gly Gly Gly Gly Ser
1               5                   10                  15

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 21

Gly Gly Gly Gly Ser
1               5

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 1-4 'Gly Gly
      Gly Gly Ser' repeating units"

<400> SEQUENCE: 22

Gly Gly Gly Gly Ser Gly Gly Gly Gly Ser Gly Gly Gly Gly Ser Gly
1               5                   10                  15

Gly Gly Gly Ser
            20

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Gly Gly Gly Gly Gly Gly Gly
1               5

<210> SEQ ID NO 24
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Gly Gly Gly Gly Gly
1               5

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(15)
<223> OTHER INFORMATION: /note="This sequence may encompass 1-3 'Glu Ala
      Ala Ala Lys' repeating units"

<400> SEQUENCE: 25

Glu Ala Ala Ala Lys Glu Ala Ala Ala Lys Glu Ala Ala Ala Lys
1               5                   10                  15
```

```
<210> SEQ ID NO 26
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (2)..(26)
<223> OTHER INFORMATION: /note="This region may encompass 2-5 'Glu Ala
      Ala Ala Lys' repeating units"

<400> SEQUENCE: 26

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 27
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Glu Ala Ala Ala Lys Glu Ala Ala Ala Lys Ala
1               5                   10

<210> SEQ ID NO 28
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Pro Ala Pro Ala Pro
1               5

<210> SEQ ID NO 30
<211> LENGTH: 18
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 30

Lys Glu Ser Gly Ser Val Ser Ser Glu Gln Leu Ala Gln Phe Arg Ser
1               5                   10                  15

Leu Asp

<210> SEQ ID NO 31
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Glu Gly Lys Ser Ser Gly Ser Gly Ser Glu Ser Lys Ser Thr
1               5                   10

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ser Ala Gly Ser Ala Ala Gly Ser Gly Glu Phe
1               5                   10

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 33

His His His His His His
1               5
```

METHODS OF GENERATING BROADLY PROTECTIVE VACCINE COMPOSITIONS COMPRISING HEMAGGLUTININ

CROSS-REFERENCE TO RELATED APPLICATIONS

This application is a national phase entry pursuant to 35 U.S.C. § 371 of International Application No. PCT/US2019/024323 filed Mar. 27, 2019, which claims the benefit of priority to U.S. Provisional Application No. 62/649,004, filed Mar. 28, 2018, the contents incorporated by reference in their entirety.

The present application contains a Sequence Listing which has been submitted electronically in ASCII format and is hereby incorporated by reference in its entirety. Said ASCII copy, created on Mar. 27, 2019, is named 01121-0036-00PCT_SL.txt and is 85,964 bytes in size.

Influenza has a long standing history of pandemics, epidemics, resurgences, and outbreaks. For example, annual influenza epidemics are thought to result in three to five million cases of severe illnesses, and about 290,000 to 650,000 deaths worldwide. Currently, vaccines provide the most effective defense against influenza. Vaccine compositions are updated annually by the World Health Organization to accommodate variations in circulating influenza strains. However, vaccine mismatches resulting from inaccurate predictions can result in significant morbidity and mortality even in vaccinated populations.

The influenza virus contains two structural glycoproteins on the surface of the viral membrane, i.e., hemagglutinin (HA) and neuraminidase (NA). HA is a homotrimeric membrane protein that binds sialic acid and is responsible for viral entry. NA is responsible for release of the virus from infected cells by the removal of sialic acid. Current influenza vaccines generally rely on the induction of neutralizing antibodies that recognize HA. However, such neutralizing antibodies are often strain specific. Thus, variability in HA (e.g., due to antigenic shift) can result in immune evasion and a decrease in vaccine effectiveness.

Accordingly, there remains a need for effective influenza vaccines that can provide broad, long-lasting (e.g., multi-season) protection against influenza viruses including mismatched strains.

SUMMARY

The present invention provides, inter alia, a cluster-based consensus (CBC) approach for generating HA polypeptides capable of eliciting a broadly reactive immune response against multiple influenza strains. In various embodiments, the method comprises:
 selecting more than one influenza HA polypeptide sequence and aligning the sequences;
 calculating pairwise similarity/dissimilarity matrices;
 identifying and creating clusters of similar sequences from the pairwise similarity/dissimilarity matrices;
 within each cluster, determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid;
 generating a first sequence comprising consensus amino acids and variable amino acids for each cluster;
 optionally, if more than one cluster is analyzed, comparing the first sequence generated from a cluster with a sequence generated in another cluster or multiple clusters by:
  aligning the sequences generated for each cluster;
  determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid; and
  generating a second sequence comprising consensus amino acids and variable amino acids;
 within the first sequence or the second sequence generated, determining a consensus amino acid for each variable amino acid position, by:
  generating a set of test sequences based on the first or second sequence, wherein test amino acids are placed at the variable amino acid positions;
  performing molecular modeling for each of the test sequences;
  determining a consensus amino acid for each variable amino acid position by selecting amino acid(s) that result in a polypeptide having a negative total energy value; and
 generating the influenza HA polypeptide comprising the consensus amino acids.

In various embodiments, the present invention provides HA polypeptides generated using methods of the invention. In exemplary embodiments, the HA polypeptides comprise the amino acid sequence of any one of SEQ ID NOs: 1-16, or a fragment thereof. In some embodiments, the present invention further relates to trimeric HA proteins comprising one or more HA polypeptides described herein.

In various embodiments, the HA polypeptides and/or the trimeric HA proteins of the invention are utilized as vaccine antigens. In some embodiments, the HA polypeptides and trimeric HA proteins provide a broadly protective immune response against multiple influenza strains, types, or subtypes. Without wishing to be bound by theory, it is believed that the HA polypeptides and trimeric HA proteins can elicit neutralizing antibody responses against multiple epitopes (e.g., conserved epitopes) within influenza viruses.

Further embodiments of the present application are as follows:

Embodiment A 1. A method for generating a recombinant influenza hemagglutinin (HA) polypeptide comprising consensus amino acids, wherein the method comprises:
 a. selecting more than one influenza HA polypeptide sequence and aligning the sequences;
 b. calculating pairwise similarity/dissimilarity matrices;
 c. identifying and creating clusters of similar sequences from the pairwise similarity/dissimilarity matrices;
 d. within each cluster, determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid;
 e. generating a first sequence comprising consensus amino acids and variable amino acids for each cluster;

f. optionally, if a plurality of clusters is analyzed, comparing the first sequence generated in step (e) of a cluster with a first sequence generated in another cluster or multiple clusters by:
   i. aligning the sequences generated in step (e) for each cluster;
   ii. determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid; and
   iii. generating a second sequence comprising consensus amino acids and variable amino acids;
g. within the first sequence generated in step (e) or the second sequence generated in step (f)(iii), determining a consensus amino acid for each variable amino acid position, by:
   i. generating a set of test sequences based on the first or second sequence, wherein test amino acids are placed at the variable amino acid positions;
   ii. performing molecular modeling for each of the test sequences;
   iii. determining a consensus amino acid for each variable amino acid position by selecting amino acid(s) that result in a polypeptide having a negative total energy value; and
h. generating the recombinant influenza HA polypeptide comprising the consensus amino acids.

Embodiment A 2. The method of embodiment A 1, wherein aligning the sequences comprises using MAFFT, MUSCLE, CLUSTAL OMEGA, FASTA, a combination thereof, or any other multiple sequence alignment software packages.

Embodiment A 3. The method of embodiment A 1 or A 2, wherein calculating the pairwise similarity/dissimilarity matrices comprises using BLOSUM, PAM, IDENTITY substitution matrices, or a combination thereof.

Embodiment A 4. The method of any one of embodiments A 1-3, wherein identifying and creating clusters of similar sequences from the pairwise similarity/dissimilarity matrices comprise using K-means clustering, minimax clustering, principle component analysis (PCA), multidimensional scaling (MDS), or a combination thereof.

Embodiment A 5. The method of any one of embodiments A 1-4, wherein molecular modeling comprises comparing to a crystal structure of an influenza HA polypeptide or protein.

Embodiment A 6. The method of any one of embodiments A 1-5, wherein molecular modeling comprises use of Rosetta or any other molecular modeling software.

Embodiment A 7. The method of any one of embodiments A 1-6, wherein the test amino acids comprise any natural or non-natural amino acid found in proteins.

Embodiment A 8. A recombinant influenza HA polypeptide generated using the method of any one of embodiments A 1-7.

Embodiment A 9. The recombinant influenza HA polypeptide of embodiment A 8, where in the polypeptide comprises an amino acid sequence selected from any one of SEQ ID NOs: 1-16, or a fragment thereof, or an amino acid sequence having at least 85%, 90%, 95%, 96%, 97%, 98%, or 99% identity to any one of SEQ ID NOs: 1-16, or a fragment thereof.

Embodiment A 10. A recombinant trimeric HA protein comprising one or more of the recombinant HA polypeptides of embodiment A 8 or A 9.

Embodiment A 11. An isolated nucleic acid encoding the recombinant HA polypeptide of embodiment A 8 or A 9 or the recombinant trimeric HA protein of embodiment A 10.

Embodiment A 12. A vector comprising the nucleic acid of embodiment A 11.

Embodiment A 13. An isolated cell comprising the vector of embodiment A 12.

Embodiment A 14. The isolated cell of embodiment A 13, wherein the cell is a mammalian cell.

Embodiment A 15. The isolated cell of embodiment A 14, wherein the isolated cell is a HEK293T cell or a CHO cell.

Embodiment A 16. The isolated cell of embodiment A 13, wherein the isolated cell is an insect cell.

Embodiment A 17. A fusion protein comprising the recombinant HA polypeptide of embodiment A 8 or A 9 or the recombinant trimeric HA protein of embodiment A 10.

Embodiment A 18. An influenza virus-like particle (VLP) comprising the recombinant HA polypeptide of embodiment A 8 or A 9 or the recombinant trimeric HA protein of embodiment A 10.

Embodiment A 19. The influenza VLP of embodiment A 18, further comprising one or more of an influenza neuraminidase (NA) protein, an influenza matrix (M1) protein, a human immunodeficiency virus (HIV) gag protein, or a combination thereof.

Embodiment A 20. A pharmaceutical composition comprising the recombinant HA polypeptide of embodiment A 8 or A 9, the recombinant trimeric HA protein of embodiment A 10, the fusion protein of embodiment A 17, or the influenza VLP of embodiment A 18 or A 19, and a pharmaceutically acceptable carrier, excipient, or adjuvant.

Embodiment A 21. The pharmaceutical composition of embodiment A 20, wherein the composition elicits an immune response against one or more influenza strains, types, and/or subtypes.

Embodiment A 22. A method of immunizing a subject against influenza virus, comprising administering to the subject an effective amount of the recombinant HA polypeptide of embodiment A 8 or A 9, the recombinant trimeric HA protein of embodiment A 10, the fusion protein of embodiment A 17, or the influenza VLP of embodiment A 18 or A 19, or the pharmaceutical composition of embodiment A 20 or A 21.

Embodiment A 23. A method of inducing an immune response to influenza virus in a subject, comprising administering to the subject an effective amount of the recombinant HA polypeptide of embodiment A 8 or A 9, the recombinant trimeric HA protein of embodiment A 10, the fusion protein of embodiment A 17, or the influenza VLP of embodiment A 18 or A 19, or the pharmaceutical composition of embodiment A 20 or A 21.

Embodiment A 24. The method of embodiment A 22 or A 23, wherein the influenza virus is a seasonal or pandemic influenza virus.

Embodiment A 25. The method of embodiment A 23 or A 24, wherein the immune response comprises production of antibodies against one or more influenza virus strains, types, or subtypes.

Embodiment A 26. The method of any one of embodiments A 22-A 25, wherein the subject is a mammal.

Embodiment A 27. The method of embodiment A 26, wherein the subject is a human.

Embodiment A 28. The method of any one of embodiments A 22-A 27, wherein the administering is performed via intramuscular, intranasal, intradermal, subcutaneous, oral, or intravenous routes.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

FIGURE LEGENDS

FIGS. 1A-1B show an exemplary cluster-based consensus (CBC) method for designing HA polypeptides. FIG. 1A depicts the generation of HA sequence clusters by Principle Components Analysis (PCA). Eight HA sequence clusters were identified and indicated as circles. FIG. 1B illustrates Tier assignments and assembly order as described in Example 1.

FIG. 3 illustrates the use of reverse genetics systems to recover influenza A viruses expressing CBC HA proteins. The successful rescue of recombinant influenza A viruses harboring Tier 1 and 2 CBC HA sequences (i.e., HAco3M, HAco4M, HAco5M, and HAcb345M) was determined by plaque assay and hemagglutinin activity.

Figure 4:
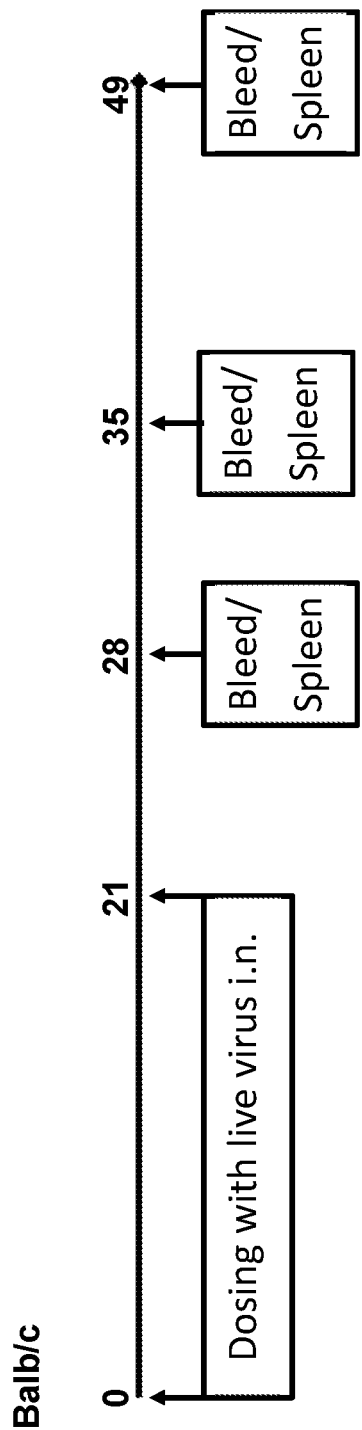

FIG. 4 provide a schematic of the immunogenicity studies described in Example 3.

FIGS. 5A-5G show that recombinant viruses expressing CBC HA sequences induced neutralizing antibody response as determined by Plaque Reduction Neutralization Tests (PRNTs).

Figure 6:
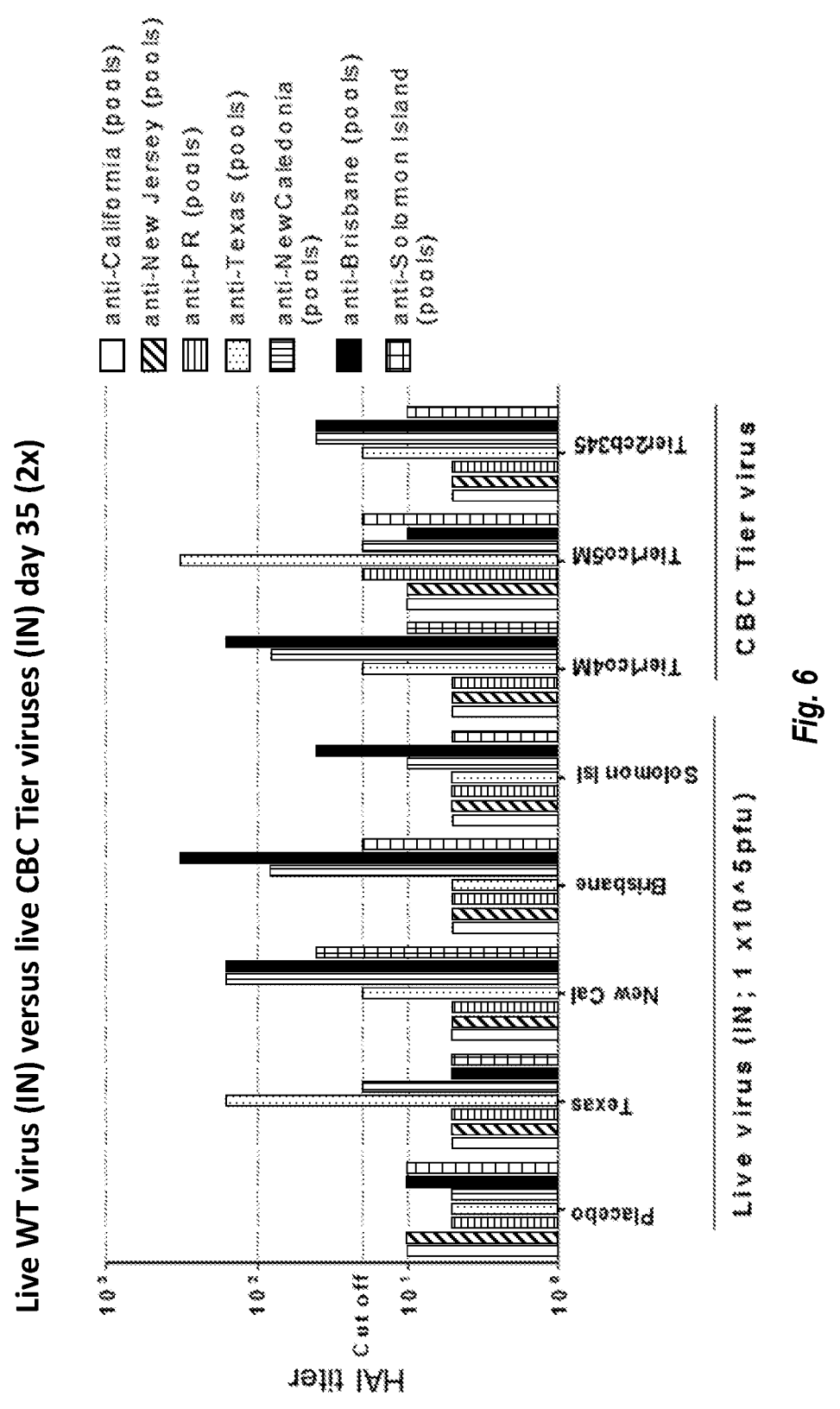

FIG. 6 shows that recombinant viruses expressing CBC HA sequences induced neutralizing antibody response as determined by hemagglutinin inhibition (HAI) assay.

Figure 7A:
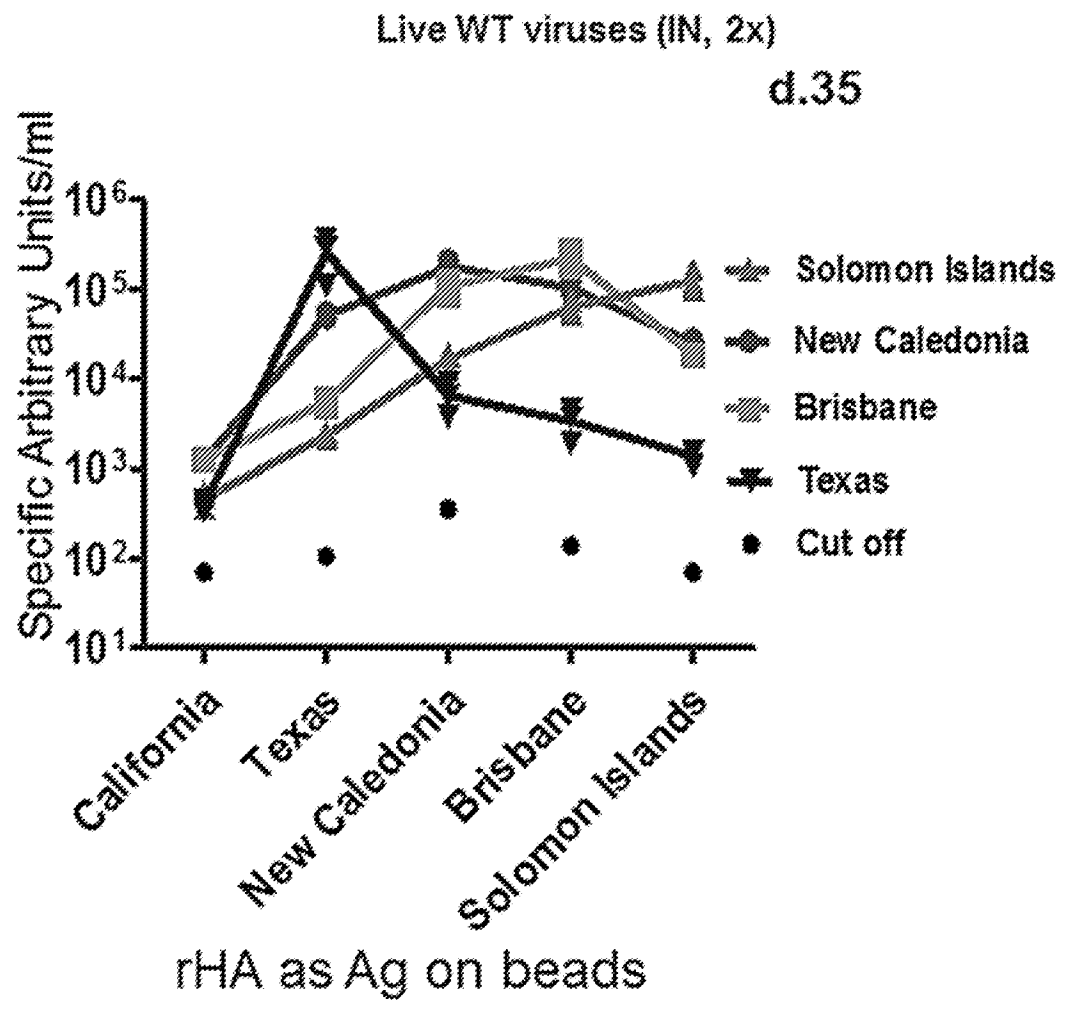
Figure 7B:
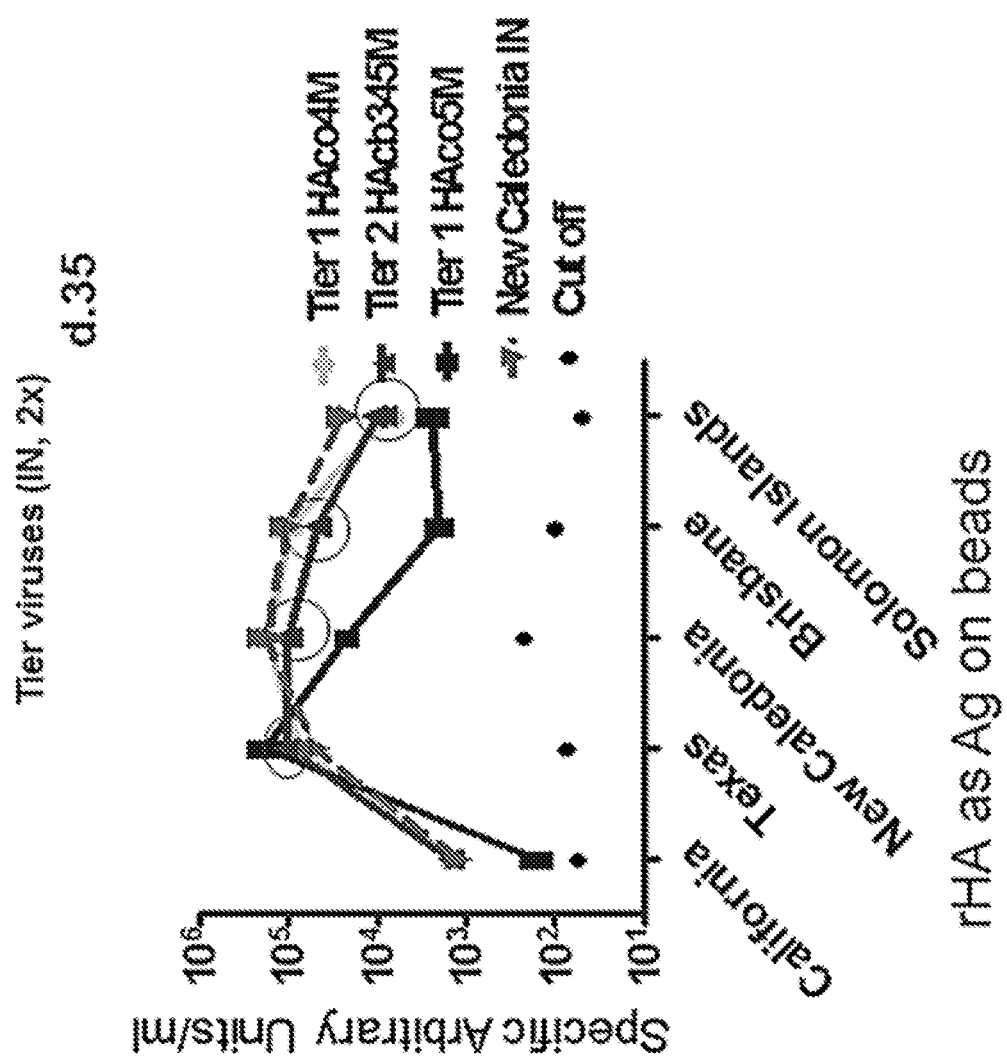
Figure 7C:
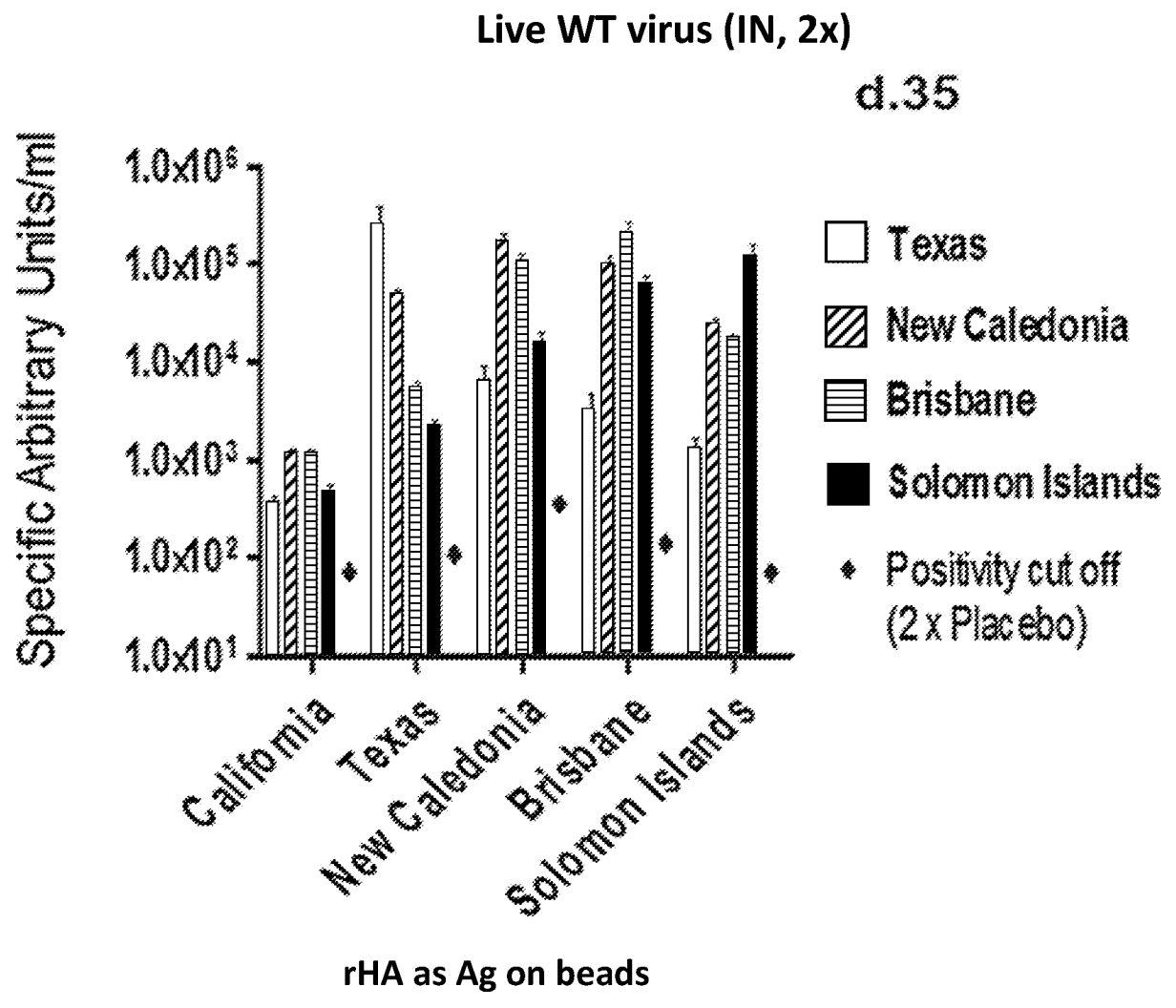
Figure 7D:
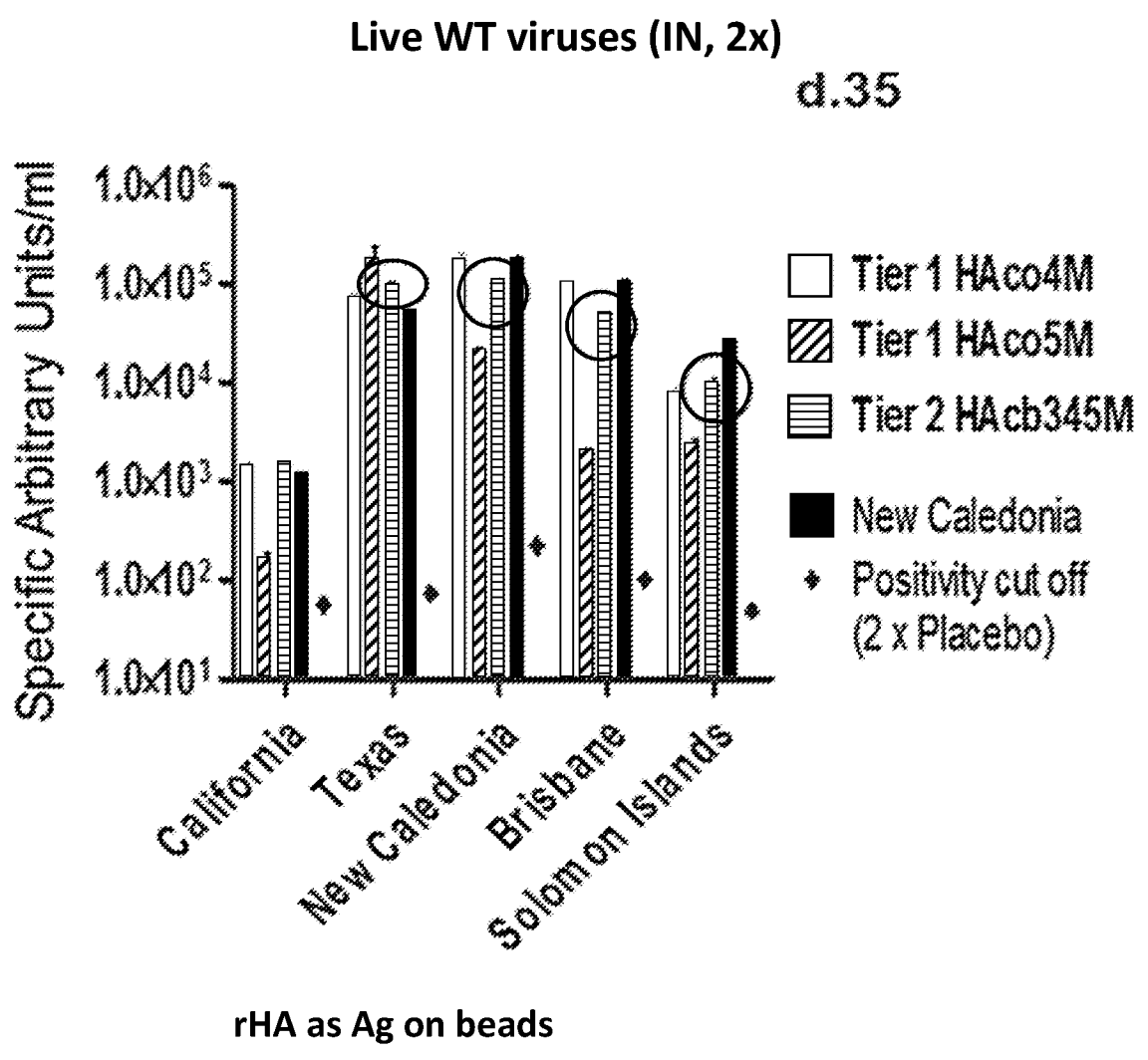

FIGS. 7A-7B show that recombinant viruses expressing CBC HA sequences induced antibody binding as determined by Antibody Forensic (AF) assay. The results are presented for wildtype viruses (FIGS. 7A and 7C) and tier viruses (FIGS. 7B and 7D).

FIG. 8 provides a schematic of the VLP immunization study described in Example 4.

Figure 9:
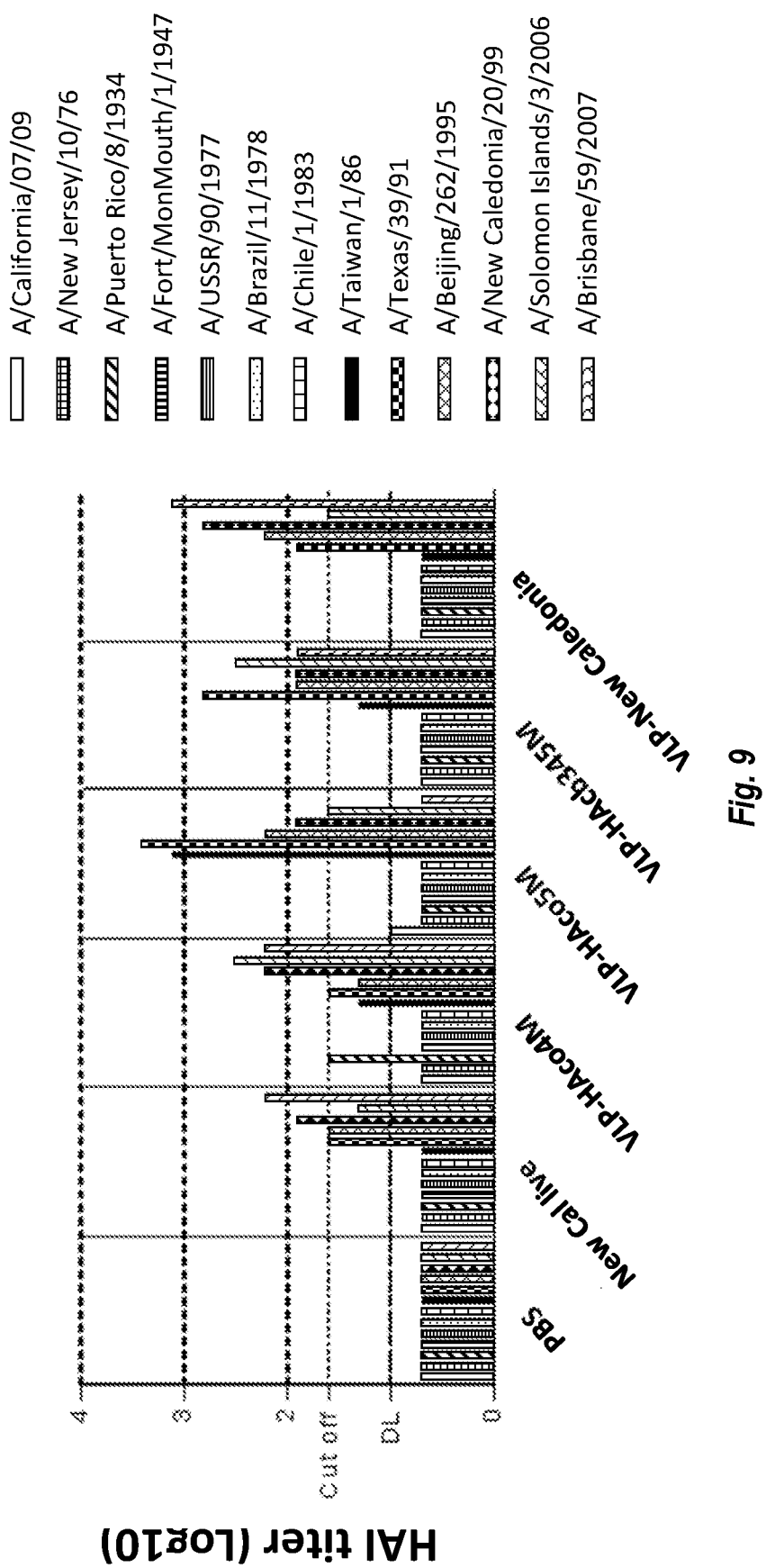

FIG. 9 shows the immunogenicity profiles of VLPs expressing various CBC HA proteins as determined by hemagglutinin inhibition (HAI) assay. Within each panel (separated by vertical lines), the viruses tested were, from left to right, A/California/07/09; A/New Jersey/10/76; A/Puerto Rico/8/1934; A/Fort/MonMouth/1/1947; A/USSR/90/1977; A/Brazil/11/1978; A/Chile/1/1983; A/Taiwan/1/86; A/Texas/36/91; A/Beijing/262/1995; A/New Caledonia/20/99; A/Solomon Islands/3/2006; and A/Brisbane/59/2007.

Figure 10:
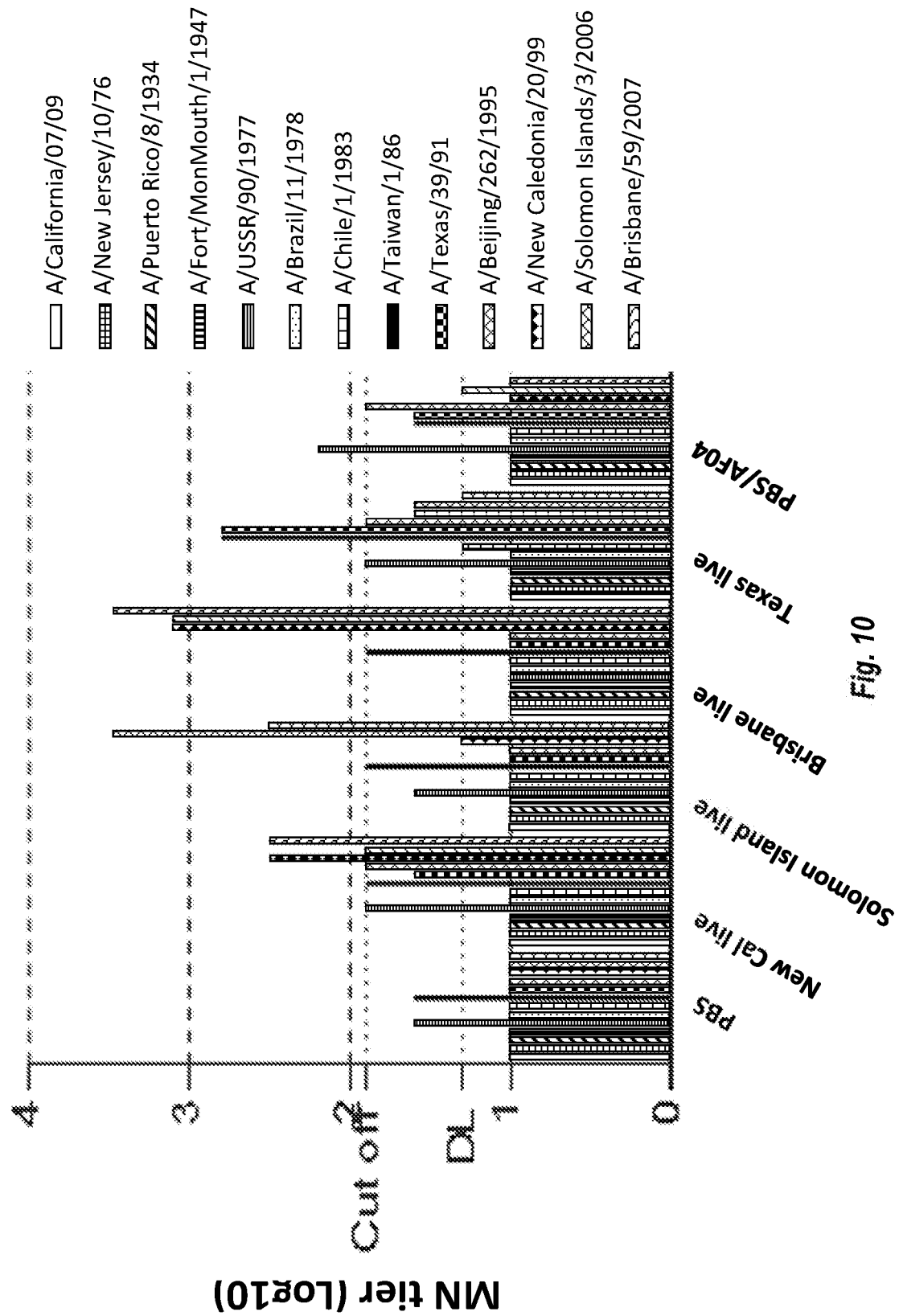
Figure 10:
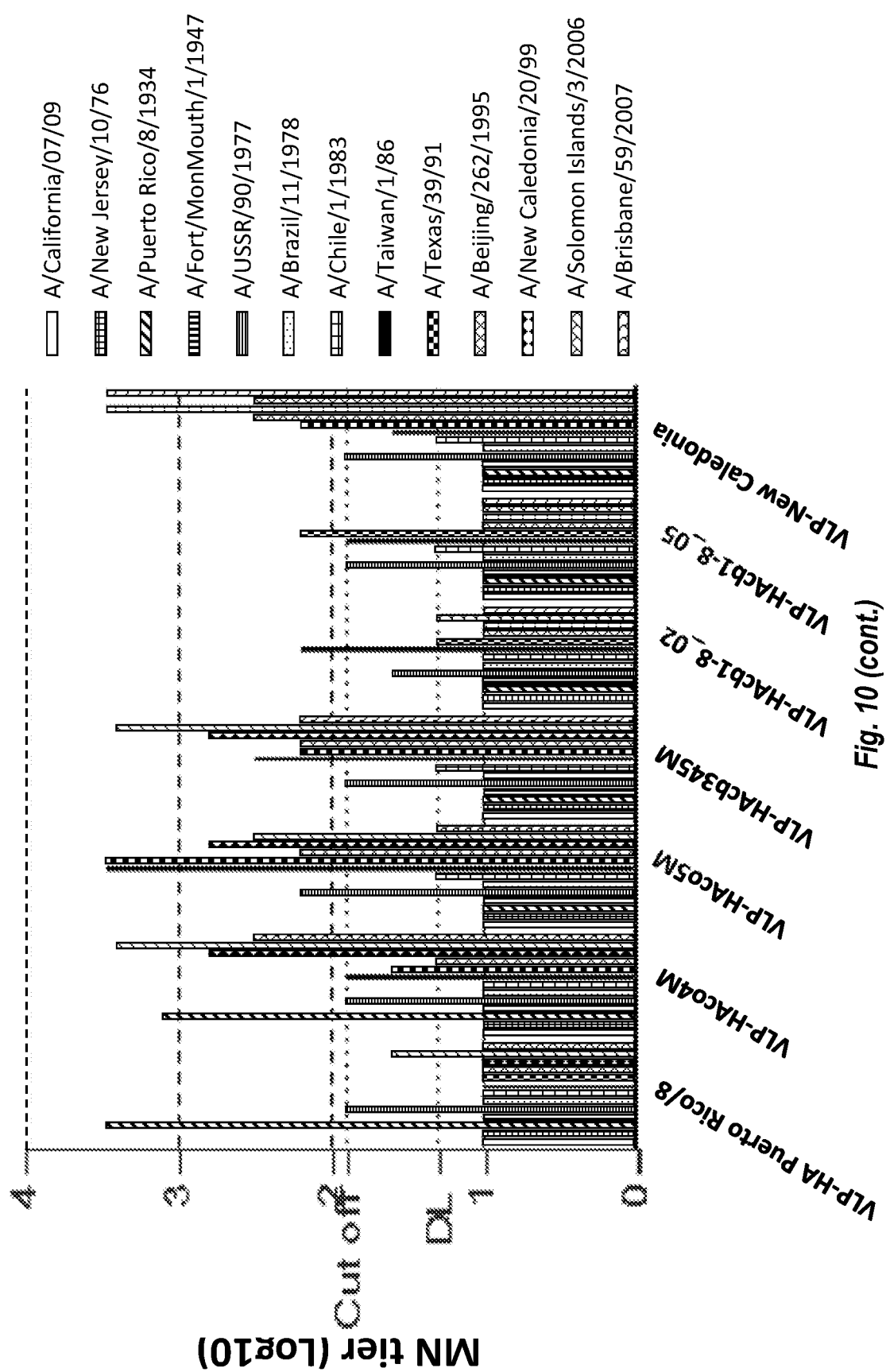

FIG. 10 shows the immunogenicity profiles of VLPs expressing various CBC HA proteins as determined by microneutralization (MN) assay. Within each panel, the viruses tested were, from left to right, A/California/07/09; A/New Jersey/10/76; A/Puerto Rico/8/1934; A/Fort/MonMouth/1/1947; A/USSR/90/1977; A/Brazil/11/1978; A/Chile/1/1983; A/Taiwan/1/86; A/Texas/36/91; A/Beijing/262/1995; A/New Caledonia/20/99; A/Solomon Islands/3/2006; and A/Brisbane/59/2007.

DESCRIPTION OF THE SEQUENCES

TABLE 1

Table of Sequences

| Description | Sequences | SEQ ID NO |
|---|---|---|
| Tier 1<br>HAco1M | MKAILVVLLYTFATANADTLCIGYHANNSTDTVDTVLEKNVTVTHSVNLLEDKHNGKLCK<br>LRGVAPLHLGKCNIAGWILGNPECESLSTASSWSYIVETSSSDNGTCYPGDFIDYEELRE<br>QLSSVSSFERFEIFPKTSSWPNHDSNKGVTAACPHAGAKSFYKNLIWLVKKGNSYPKLSK<br>SYINDKGKEVLVLWGIHHPSTSADQQSLYQNADAYVFVGTSRYSKKFKPEIAIRPKVRDQ<br>EGRMNYYWTLVEPGDKITFEATGNLVVPRYAFAMERNAGSGIIISDTPVHDCNTTCQTPK<br>GAINTSLPFQNIHPITIGKCPKYVKSTKLRLATGLRNVPSIQSRGLFGAIAGFIEGGWTG<br>MVDGWYGYHHQNEQGSGYAADLKSTQNAIDEITNKVNSVIEKMNTQFTAVGKEFNHLEKR<br>IENLNKKVDDGFLDIWTYNAELLVLLENERTLDYHDSNVKNLYEKVRSQLKNNAKEIGNG<br>CFEFYHKCDNTCMESVKNGTYDYPKYSEEAKLNREEIDGVKLESTRIYQILAIYSTVASS<br>LVLVVSLGAISFWMCSNGSLQCRICI | 1 |
| Tier 1<br>HAco2M | MKAILVVLLYTFATANADTLCIGYHANNSTDTVDTVLEKNVTVTHSVNLLEDRHNGKLCK<br>LRGVAPLHLGKCNIAGWLLGNPECELLFTASSWSYIVETSNSDNGTCYPGDFINYEELRE<br>QLSSVSSFERFEIFPKASSWPNHETNRGVTAACPYAGANSFYRNLIWLVKKGNSYPKLSK<br>SYVNNKGKEVLVLWGIHHPPTSTDQQSLYQNADAYVFVGSSKYNKKFKPEIATRPKVRGQ<br>AGRMNYYWTLIEPGDTITFEATGNLVVPRYAFAMKRGSGSGIIISDAPVHDCNTTCQTPK<br>GAINTSLPFQNIHPVTIGECPKYVKSTKLRMATGLRNIPSIQSRGLFGAIAGFIEGGWTG<br>MIDGWYGYHHQNEQGSGYAADQKSTQNAIDGITNKVNSVIEKMNTQFTAVGKEFNHLEKR<br>IENLNKKVDDGELDIWTYNAELLVLLENERTLDYHDSNVKNLYEKVRSQLKNNAKEIGNG<br>CFEFYHKCDDTCMESVKNGTYDYPKYSEESKLNREKIDGVKLESMGVYQILAIYSTVASS<br>LVLLVSLGAISFWMCSNGSLQCRICI | 2 |
| Tier 1<br>HAco3M | MKVKLLVLLCTFTATYADTICIGYHANNSTDTVDTVLEKNVTVTHSVNLLENSHNGKLCL<br>LKGIAPLQLGNCSVAGWILGNPECELLISKESWSYIVEKPNPENGTCYPGHFADYEELRE<br>QLSSVSSFERFEIFPKESSWPNHTVTGVSASCSHNGESSFYRNLLWLTGKNGLYPNLSKS<br>YANNKEKEVLVLWGVHHPPNIGDQKTLYHTENAYVSVVSSHYSRKFTPEIAKRPKVRDQE<br>GRINYYWTLLEPGDTIIFEANGNLIAPRYAFALSRGFGSGIINSNAPMDKCDAKCQTPQG | 3 |

TABLE 1-continued

Table of Sequences

| Description | Sequences | SEQ ID NO |
|---|---|---|
| | AINSSLPFQNVHPVTIGECPKYVRSAKLRMVTGLRNIPSIQSRGLFGAIAGFIEGGWTGM<br>VDGWYGYHHQNEQGSGYAADQKSTQNAINGITNKVNSVIEKMNTQFTAVGKEFNKLERRM<br>ENLNKKVDDGFIDIWTYNAELLVLLENERTLDFHDSNVKNLYEKVKSQLKNNAKEIGNGC<br>FEFYHKCNDECMESVKNGTYDYPKYSEESKLNREKIDGVKLESMGVYQILAIYSTVASSL<br>VLLVSLGAISFWMCSNGSLQCRICI | |
| Tier 1<br>HAco4M | MKVKLLVLLCTFTATYADTICIGYHANNSTDTVDTVLEKNVTVTHSVNLLEDSHNGKLCL<br>LKGIAPLQLGNCSVAGWILGNPECELLISKESWSYIVETPNPENGTCYPGYFADYEELRE<br>QLSSVSSFERFEIFPKESSWPNHTVTGVSASCSHNGKSSFYRNLLWLTGKNGLYPNLSKS<br>YANNKEKEVLVLWGVHHPPNIGDQRALYHTENAYVSVVSSHYSRRFTPEIAKRPKVRDQE<br>GRINYYWTLLEPGDTIIFEANGNLIAPRFAFALSRGEGSGIIITSNAPMDECDAKCQTPQG<br>AINSSLPFQNVHPVTIGECPKYVRSAKLRMVTGLRNIPSIQSRGLFGAIAGFIEGGWTGM<br>VDGWYGYHHQNEQGSGYAADQKSTQNAINGITNKVNSVIEKMNTQFTAVGKEFNKLERRM<br>ENLNKKVDDGELDIWTYNAELLVLLENERTLDFHDSNVKNLYEKVKSQLKNNAKEIGNGC<br>FEFYHKCNDECMESVKNGTYDYPKYSEESKLNRERIDGVKLESMGVYQILAIYSTVASSL<br>VLLVSLGAISFWMCSNGSLQCRICI | 4 |
| Tier 1<br>HAco5M | MKVKLLVLLCAFTATYADTICIGYHANNSTDTVDTVLEKNVTVTHSVNLLEDSHNGKLCR<br>LKGTAPLQLGNCSVAGWILGNPECESLFSKESWSYIAETPNPENGTCYPGYFADYEELRE<br>QLSSVSSFERFEIFPKESSWPNHTVTKGVTASCSHNGKSSFYKNLLWLTEKNGLYPNLSK<br>SYVNNKEKEVLVLWGVHHPSNIGDQRAIYHTENAYVSVVSSHYSRRFTPEIAKRPKVRDQ<br>EGRINYYWTLLEPGDTIIFEANGNLIAPWYAFALSRGFGSGIIITSNASMGECDAKCQTPQ<br>GAINSSLPFQNVHPVTIGECPKYVRSTKLRMVTGLRNIPSIQSRGLFGAIAGFIEGGWTG<br>MIDGWYGYHHQNEQGSGYAADQKSTQNAIDGITNKVNSVIEKMNTQFTAVGKEFNKLERR<br>MENLNKKVDDGFLDIWTYNAELLVLLENERTLDFHDSNVKNLYEKVKNQLKNNAKEIGNG<br>CFEFYHKCNNECMESVKNGTYDYPKYSEESKLNREKIDGVKLESMGVYQILAIYSTVASS<br>LVLLVSLGAISFWMCSNGSLQCRICI | 5 |
| Tier 1<br>HAco6M | MKAKLLVLLCTFTATYADTICIGYHANNSTDTVDTVLEKNVTVTHSVNLLEDSHNGKLCR<br>LKGIAPLQLGKCSIAGWILGNPECESLFSKKSWSYIAETPNSENGTCYPGYFADYEELRE<br>QLSSVSSFERFEIFPKERSWPKHNVTRGVTASCSHKGKSSFYRNLLWLTEKNGSYPNLSK<br>SYVNNKEKEVLVLWGVHHPSNIEDQKTIYRKENAYVSVVSSNYNRRFTPEIAKRPKVRGQ<br>EGRINYYWTLLEPGDTIIFEANGNLIAPWYAFALSRGFGSGIIITSNASMDECDAKCQTPQ<br>GAINSSLPFQNVHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKR<br>MENLNKKVDDGFLDIWTYNAELLVLLENERTLDFHDSNVKNLYEKVKSQLKNNAKEIGNG<br>CFEFYHKCNNECMESVKNGTYDYPKYSEESKLNREKIDGVKLESMGVYQILAIYSTVASS<br>LVLLVSLGAISFWMCSNGSLQCRICI | 6 |
| Tier 1<br>HAco7M | MKAKLLVLLCTFTATYADTICIGYHANNSTDTVDTVLEKNVTVTHSVNLLEDSHNGKLCR<br>LKGIAPLQLGKCNIAGWILGNPECESLLSNRSWSYIAETPNSENGTCYPGDFADYEELRE<br>QLSSVSSFERFEIFPKERSWPKHNTTRGVTAACSHAKKSSFYRNLLWLTEKNGSYPNLSR<br>SYVNNKEKEVLVLWGVHHPSNIEDQRTLYRKENAYVSVVSSNYNRRFTPEIAERPKVRGQ<br>AGRMNYYWTLLEPGDTIIFEANGNLIAPWYAFALSRGLGSGIIITSNASMDECDTKCQTPQ<br>GAINSSLPFQNIHPVTIGECPKYVRSTKLRMVTGLRNIPSIQSRGLFGAIAGFIEGGWTG<br>MMDGWYGYHHQNEQGSGYAADQKSTQNAINGITNKVNSVIEKMNTQFTAVGKEFNKLEKR<br>MENLNKKVDDGFLDIWTYNAELLVLLENERTLDFHDSNVKNLYEKVKNQLRNNAKEIGNG<br>CFEFYHKCDNECMESVKNGTYDYPKYSEESKLNREKIDGVKLESMGVYQILAIYSTVASS<br>LVLLVSLGAISFWMCSNGSLQCRICI | 7 |
| Tier 1<br>HAco8M | MKAKLLVLLCTFTATYADTICIGYHANNSTDTVDTVLEKNVTVTHSVNLLEDSHNGKLCR<br>LKGIAPLQLGKCNIAGWLLGNPECDSLLPARSWSYIVETPNSENGICYPGDFIDYEELRE<br>QLSSVSSFERFEIFPKESSWPNHTTNGVTAACSHEGKSSFYRNLLWLTKKEGSYPKLKN<br>SYVNKKGKEVLVLWGVHHPSNSKEQQNLYQNENAYVSVVSSNYNRRFTPEIAERPKVRDQ<br>AGRMNYYWTLLKPGDTIIFEANGNLIAPWYAFALSRGFGSGIIITSNASMHECNTKCQTPL<br>GAINSSLPFQNIHPVTIGECPKYVRSAKLRMVTGLRNIPSIQSRGLFGAIAGFIEGGWTG<br>MIDGWYGYHHQNEQGSGYAADQKSTQNAINGITNKVNSVIEKMNTQFTAVGKEFNNLEKR<br>MENLNKKVDDGFLDIWTYNAELLVLLENERTLDFHDSNVKNLYEKVKSQLKNNAKEIGNG<br>CFEFYHKCDNECMESVRNGTYDYPKYSEESKLNREKIDGVKLESMGVYQILAIYSTVASS<br>LVLLVSLGAISFWMCSNGSLQCRICI | 8 |
| Tier 2<br>HAcb12M | MKAILVVLLYTFATANADTLCIGYHANNSTDTVDTVLEKNVTVTHSVNLLEDKHNGKLCKLRGVAPLHLGKC<br>NIAGWLLGNPECESLFTASSWSYIVETSNSDNGTCYPGDFINYEELREQLSSVSSFERFEIFPKTSSWPNHD<br>TNRGVTAACPHAGAKSFYRNLIWLVKKGNSYPKLSKSYINDKGKEVLVLWGIHHPSTSADQQSLYQNADAYV<br>FVGSSKYSKKFKPEIATRPKVRDQAGRMNYYWTLVEPGDTITFEATGNLVVPRYAFAMKRGSGSGIIISDTP<br>VHDCNTTCQTPKGAINTSLPFQNIHPVTIGECPKYVKSTKLRMATGLRNVPSIQSRGLFGAIAGFIEGGWTG<br>MVDGWYGYHHQNEQGSGYAADQKSTQNAIDGITNKVNSVIEKMNTQFTAVGKEFNHLEKRIENLNKKVDDGF<br>LDIWTYNAELLVLLENERTLDYHDSNVKNLYEKVRSQLKNNAKEIGNGCFEFYHKCDNTCMESVKNGTYDYP<br>KYSEEAKLNREEIDGVKLESTRIYQILAIYSTVASSLVLVVSLGAISFWMCSNGSLQCRICI | 9 |
| Tier 2<br>HAcb67M | MKAKLLVLLCALSATDADTICIGYHANNSTDTVDTVLEKNVTVTHSVNLLEDSHNGKLCRLKGIAPLQLGKC<br>SIAGWILGNPECESLFSKKSWSYIAETPNSENGTCYPGYFADYEELREQLSSVSSFERFEIFPKERSWPKHN<br>ITRGVTAACSHKGKSSFYRNLLWLTEKNGSYPNLSKSYVNNKEKEVLVLWGVHHPSNIEDQKTLYRKENAYV<br>SVVSSNYNRRFTPEIAKRPKVRGQEGRINYYWTLLEPGDTIIFEANGNLIAPWYAFALSRGFGSGIITSNAS<br>MDECDTKCQTPQGAINSSLPFQNVHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF | 10 |

TABLE 1-continued

| Table of Sequences | | |
|---|---|---|
| Description | Sequences | SEQ ID NO |
| | LDIWTYNAELLVLLENERTLDFHDSNVKNLYEKVKNQLKNNAKEIGNGCFEFYHKCNNECMESVKNGTYDYP<br>KYSEESKLNREKIDGVKLESMGVYQILAIYSTVASSLVLLVSLGAISFWMCSNGSLQCRICI | |
| Tier 2<br>HAcb345M | MKVKLLVLLCTFTATYADTICIGYHANNSTDTVDTVLEKNVTVTHSVNLLEDSHNGKLCLLKGIAPLQLGNC<br>SVAGWILGNPECELLISKESWSYIVETPNPENGTCYPGYFADYEELREQLSSVSSFERFEIFPKESSWPNHT<br>VTGVSASCSHNGKSSFYRNLLWLTGKNGLYPNLSKSYTNNKEKEVLVLWGVHHPPNIGDQRALYHTENAYVS<br>VVSSHYSRRFTPEIAKRPKVRDQEGRINYYWTLLEPGDTIIFEANGNLIAPRYAFALSRGFGSGIITSNAPM<br>DECDAKCQTPQGAINSSLPFQNVHPVTIGECPKYVRSAKLRMVTGLRNIPSIQSRGLFGAIAGFIEGGWTGM<br>VDGWYGYHHQNEQGSGYAADQKSTQNAINGITNKVNSVIEKMNTQFTAVGKEFNKLERRMENLNKKVDDGFL<br>DIWTYNAELLVLLENERTLDFHDSNVKNLYEKVKSQLKNNAKEIGNGCFEFYHKCNDECMESVKNGTYDYPK<br>YSEESKLNREKIDGVKLESMGVYQILAIYSTVASSLVLLVSLGAISFWMCSNGSLQCRICI | 11 |
| Tier 3<br>HAcb1-8_01 | MKAKLLVLLCTFTATYADTICIGYHANNSTDTVDTVLEKNVTVTHSVNLLEDSHNGKLCRLKGIAPLQLGKC<br>NIAGWILGNPECESLFSKESWSYIVETPNSENGTCYPGDFADYEELREQLSSVSSFERFEIFPKESSWPNHN<br>TTRGVTAACSHNGKSSFYRNLLWLTKKNGSYPNLSKSYVNNKEKEVLVLWGVHHPSNIGDQQTLYQNENAYV<br>SVVSSNYSRRFTPEIAKRPKVRDQEGRMNYYWTLLEPGDTIIFEANGNLIAPRYAFALSRGFGSGIITSNAS<br>MDECDTKCQTPQGAINSSLPFQNIHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF<br>LDIWTYNAELLVLLENERTLDFHDSNVKNLYEKVKSQLKNNAKEIGNGCFEFYHKCDNECMESVKNGTYDYP<br>KYSEEAKLNREEIDGVKLESMGVYQILAIYSTVASSLVLLVSLGAISFWMCSNGSLQCRICI | 12 |
| Tier 3<br>HAcb1-8_02 | MKAKLLVLLCTFTATYADTICIGYHANNSTDTVDTVLEKNVTVTHSVNLLEDSHNGKLCRLKGIAPLQLGKC<br>NIAGWILGNPECESLFSKESWSYIVETPNSENGTCYPGDFADYEELREQLSSVSSFERFEIFPKESSWPNHN<br>TTRGVTAACSHNGKSSFYRNLLWLTKKNGSYPNLSKSYVNNKEKEVLVLWGVHHPSNIGDQQTLYQNENAYV<br>SVVSSNYSRRFTPEIAKRPKVRDQEGRMNYYWTLLEPGDTIIFEANGNLIAPRYAFALSRGFGSGIITSNAP<br>MDECDTKCQTPQGAINSSLPFQNIHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF<br>LDIWTYNAELLVLLENERTLDFHDSNVKNLYEKVKSQLKNNAKEIGNGCFEFYHKCDNECMESVKNGTYDYP<br>KYSEEAKLNREEIDGVKLESMGVYQILAIYSTVASSLVLLVSLGAISFWMCSNGSLQCRICI | 13 |
| Tier 3<br>HAcb1-8_03 | MKAKLLVLLCTFTATYADTICIGYHANNSTDTVDTVLEKNVTVTHSVNLLEDSHNGKLCRLKGIAPLQLGKC<br>NIAGWILGNPECESLFSKESWSYIVETPNSENGTCYPGDFADYEELREQLSSVSSFERFEIFPKESSWPNHN<br>TTRGVTAACSHNGKSSFYRNLLWLTKKNGSYPNLSKSYVNNKEKEVLVLWGVHHPSNIGDQQTLYQNENAYV<br>SVVSSNYSRRFTPEIAKRPKVRDQEGRMNYYWTLLEPGDTIIFEANGNLIAPWYAFALSRGFGSGIITSNAS<br>MDECDTKCQTPQGAINSSLPFQNIHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF<br>LDIWTYNAELLVLLENERTLDFHDSNVKNLYEKVKSQLKNNAKEIGNGCFEFYHKCDNECMESVKNGTYDYP<br>KYSEEAKLNREEIDGVKLESMGVYQILAIYSTVASSLVLLVSLGAISFWMCSNGSLQCRICI | 14 |
| Tier 3<br>HAcb1-8_04 | MKAKLLVLLCTFTATYADTICIGYHANNSTDTVDTVLEKNVTVTHSVNLLEDSHNGKLCRLKGIAPLQLGKC<br>NIAGWILGNPECESLFSKESWSYIVETPNSENGTCYPGDFADYEELREQLSSVSSFERFEIFPKESSWPNHN<br>VTRGVTAACSHNGKSSFYRNLLWLTKKNGSYPNLSKSYVNNKEKEVLVLWGVHHPSNIGDQQTLYQNENAYV<br>SVVSSNYSRRFTPEIAKRPKVRDQEGRMNYYWTLLEPGDTIIFEANGNLIAPRYAFALSRGFGSGIITSNAS<br>MDECDTKCQTPQGAINSSLPFQNIHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF<br>LDIWTYNAELLVLLENERTLDFHDSNVKNLYEKVKSQLKNNAKEIGNGCFEFYHKCDNECMESVKNGTYDYP<br>KYSEEAKLNREEIDGVKLESMGVYQILAIYSTVASSLVLLVSLGAISFWMCSNGSLQCRICI | 15 |
| Tier 3<br>HAcb1-8_05 | MKAKLLVLLCTFTATYADTICIGYHANNSTDTVDTVLEKNVTVTHSVNLLEDSHNGKLCRLKGIAPLQLGKC<br>NIAGWILGNPECESLFSKESWSYIVETPNSENGTCYPGDFADYEELREQLSSVSSFERFEIFPKESSWPNHN<br>VTRGVTAACSHNGKSSFYRNLLWLTKKNGSYPNLSKSYVNNKEKEVLVLWGVHHPSNIGDQQTLYQNENAYV<br>SVVSSNYSRRFTPEIAKRPKVRDQEGRMNYYWTLLEPGDTIIFEANGNLIAPWYAFALSRGFGSGIITSNAS<br>MDECDTKCQTPQGAINSSLPFQNIHPVTIGECPKYVRSTKLRMVTGLRNIPSIQSRGLFGAIAGFIEGGWTG<br>MIDGWYGYHHQNEQGSGYAADQKSTQNAINGITNKVNSVIEKMNTQFTAVGKEFNKLEKRMENLNKKVDDGF<br>LDIWTYNAELLVLLENERTLDFHDSNVKNLYEKVKSQLKNNAKEIGNGCFEFYHKCDNECMESVKNGTYDYP<br>KYSEEAKLNREEIDGVKLESMGVYQILAIYSTVASSLVLLVSLGAISFWMCSNGSLQCRICI | 16 |
| N-terminal CD5-<br>derived secretion<br>signal | MPMGSLQPLATLYLLGMLVASVL | 17 |
| Strep-tag | WSHPQFEK | 18 |

DETAILED DESCRIPTION

Definitions

Adjuvant: As used herein, an adjuvant refers to a substance or vehicle that non-specifically enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists and costimulatory molecules. Exemplary biological adjuvants include, but are not limited to, IL-2, RANTES, GM-CSF, TNF-α, IFN-γ, G-CSF, LFA-3, CD72, B7-1, B7-2, OX-40L, 41 BBL, or combinations thereof.

Antibody: As used herein, an antibody refers to a protein or a polypeptide that includes canonical immunoglobulin sequence elements sufficient to confer specific binding to a particular antigen. In some embodiments, the antibody is a classic antibody comprising two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, antibody also refers to an "antibody fragment" or "antibody fragments," which include a portion of an intact antibody, such as, for example, the antigen-binding or variable region of an antibody. Examples of "antibody fragments" include Fab, Fab', F(ab')2, Fv fragments, triabodies, tetrabodies, linear antibodies, single-chain antibody molecules, and CDR-containing moieties included in multispecific antibodies. In certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, the antibody is a chimeric antibody. In some embodiments, the antibody is humanized.

Antigen: As used herein, an antigen refers to an agent that elicits an immune response, and/or an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism. Alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments, an influenza HA polypeptide or immunogenic fragment thereof is an antigen.

Antigenic drift: As used herein, antigenic drift refers to mutations in HA or NA antigens that occur relatively often. Antigenic drift can enable the influenza virus to evade immune recognition and may decrease vaccine efficacy.

Antigenic shift: As used herein, antigenic shift refers to major changes in HA or NA antigens caused by reassortment of genetic material between different influenza strains.

Approximately: As used herein, the term "approximately" or "about," as applied to one or more values of interest, refers to a value that is similar to a stated reference value. In certain embodiments, the term "approximately" or "about" refers to a range of values that fall within about 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Epitope: As used herein, refers to any moiety that is specifically recognized by an immunoglobulin (e.g., antibody or receptor) binding component in whole or in part. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some of the chemical atoms or groups are physically separated from one another when the antigen adopts an alternative conformation (e.g., is linearized).

Head Region: As used herein, the term "head region" refers to a membrane distal globular shaped domain of influenza HA protein. The HA head region mediates receptor binding and is present within the HA1 subunit of the HA protein.

Hemagglutinin or HA protein: As used herein, hemagglutinin or HA protein refers to an integral membrane glycoprotein on the surface of the influenza viral membrane. Specifically, the HA protein is usually expressed as a homotrimeric complex on the surface of influenza virions. Individual HA monomeric polypeptides can be further segregated into the membrane distal globular head region and the membrane proximal stem region. The HA protein is responsible for mediating virus attachment and subsequent membrane fusion with target cells. Currently, there are at least 18 known HA subtypes (i.e., H1, H2, H3, H4, H5, H6, H7, H8, H9, H10, H11, H12, H13, H14, H15, H16, H17, and H18) which are defined by their interaction with antibodies. Humans are generally infected by viruses of the H1, H2, and H3 subtypes. In some embodiments, the HA protein may be monomeric and comprises a single HA polypeptide. In other embodiments, the HA protein is trimeric and comprises three HA polypeptides. As used herein, "hemagglutinin polypeptide" or "HA polypeptide" refers to a polypeptide whose amino acid sequence includes at least one characteristic sequence of HA. HA polypeptides can include full length influenza HA polypeptide sequences and fragments thereof. Those of ordinary skill in the art can readily identify sequences that are characteristic of HA polypeptides generally, and/or of particular HA polypeptides (e.g., H1, H2, or H3 polypeptides), or of HAs that mediate infection of particular hosts (e.g., avian, camel, canine, cat, civet, equine, human, leopard, mink, mouse, seal, stone martin, swine, tiger, whale, etc.). The National Center for Biotechnology Information (NCBI) maintains a database of HA polypeptide sequences.

Host: As used herein, the term "host" refers to a system (e.g., a cell, an organism, etc.) in which a polypeptide of interest is present. In some embodiments, a host is a system that is susceptible to infection with a particular infectious agent. In some embodiments, a host is a system that expresses a particular polypeptide or protein of interest.

Host cell: As used herein, "host cell" refers to a cell into which exogenous DNA (recombinant or otherwise) has been introduced. For example, host cells may be used to produce the influenza HA polypeptides described herein by standard recombinant techniques. Persons skilled in the art understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include prokaryotic or eukaryotic cells (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions (e.g., hybridomas or quadromas). In some embodiments, the cell is a human, monkey, ape, hamster, rat, or mouse cell. In some embodiments, the cell is eukaryotic and is selected from, but not limited to, CHO (e.g., CHO K1, DXB-11 CHO, Veggie-CHO), COS (e.g., COS-7), retinal cell, Vero, CV1, kidney cell (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER. C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable of, under appropriate conditions, stimulating an immune response, such as the production of antibodies or a T cell response in an animal, including compositions that are injected or absorbed into an animal. As used herein, an "immunogenic composition" is a composition comprising an immunogen (such as an HA polypeptide or a trimeric HA protein). As used herein, "immunize" means to render a subject protected from an infectious disease, such as by vaccination.

Influenza virus: As used herein, refers to a segmented negative-strand RNA virus that belongs to the Orthomyxoviridae family.

Influenza vaccine: As used herein, refers to an immunogenic composition capable of stimulating an immune response, administered for the prevention, amelioration, or treatment of influenza virus infection. An influenza vaccine may include, for example, attenuated or killed (e.g., split) influenza virus, virus-like particles (VLPs) and/or antigenic polypeptides or proteins (e.g., the HA polypeptides or trimeric HA proteins described herein) or DNA derived from them, or any recombinant versions of such immunogenic materials. Influenza vaccines also include DNA and viral vector based vaccines. Vaccines contemplated herein may optionally include one or more adjuvants.

Isolated: As used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In exemplary embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Outbreak: As used herein, an influenza virus "outbreak" refers to a collection of virus isolates from within a single country in a given year.

Pandemic, seasonal, swine strains: As used herein, a "pandemic" influenza strain is one that has caused or has capacity to cause pandemic infection of human populations. In some embodiments, a pandemic strain has caused pandemic infection. In some embodiments, such pandemic infection involves epidemic infection across multiple territories. In some embodiments, pandemic infection involves infection across territories that are separated from one another (e.g., by mountains, bodies of water, as part of distinct continents, etc.) such that infections ordinarily do not pass between them. In some embodiments, pandemic influenza strains include those arising from reassortment (antigenic shift occurring approximately every 20-30 years) between human and avian or swine influenza viruses that result in a virus with a novel HA or NA of avian or swine origin, against which humans lack immunity. In other words, the human population is considered to be naive, having no or little resistance either as a result of prior vaccination or prior exposure. Pandemic and seasonal strains are antigenically distinct and by sequence quite different. In general, seasonal influenza strains may be defined as circulating strains from a particular season or a particular year, for example, 1986 through to 2009 (including 2009 sequences that are not pandemic) and other strains that have substantially similar genetic sequences encoding antigenic regions (i.e., similar in antigenic sequence space). Swine influenza strains refer to any influenza strain that is related to viruses endemic in pigs. Exemplary pandemic strains include, without limitation, A/California/07/2009, A/California/04/2009, A/Belgium/145/2009, A/South Carolina/01/1918, and A/New Jersey/1976. Pandemic subtypes include, in particular, the H5N1, H2N2, H9N2, H7N7, H7N3, H7N9 and H10N7 subtypes. Exemplary seasonal strains include, without limitation, A/Puerto Rico/8/1934, A/Fort Monmouth/1/1947, A/Chile/1/1983, A/Texas/36/1991, A/Singapore/6/1986, A/Beijing/32/1992, A/New Caledonia/20/1999, A/Solomon Islands/03/2006, and A/Brisbane/59/2007. Exemplary swine strains include, without limitation, A/New Jersey/1976 isolates and A/California/07/2009. Additional influenza pandemic, seasonal, and/or swine strains are known in the art.

Prevention: As used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Recombinant: As used herein, the term "recombinant" is intended to refer to polypeptides or proteins (e.g., HA polypeptides or trimeric HA proteins as described herein) that are designed, engineered, prepared, expressed, created, or isolated by recombinant means, such as polypeptides expressed using a recombinant expression vector transfected into a host cell, polypeptides isolated from a recombinant, combinatorial polypeptide library, or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same polypeptide (e.g., two epitopes from two separate HA polypeptides).

Stem Region: As used herein, the term "stem region" or "stalk region" refers to a membrane proximal, elongated domain that emerges from the globular head domain of influenza HA protein. The stem region mediates membrane fusion and is composed of sequence regions of the HA1 and HA2 subunits of the HA protein.

Signal sequence, secretion signal, or secretion signal peptide: the terms as used herein, refers to a peptide sequence that signals for secretion from a cell. A secretion signal can lead to secretion of a polypeptide or protein that would otherwise not be secreted.

Trimerization domain: the term as used herein refers to an amino acid sequence encoding a domain that causes the trimeric assembly of a polypeptide or protein. A trimerization domain that is not native to a particular protein may be termed an artificial or a heterologous trimerization domain. Exemplary trimerization domains include, but are not limited to, the trimerization domain of collagen, a GCN4-based isoleucine zipper, an HIV gp41 trimerization domain, or the T4 bacteriophage fibritin foldon (Fd) trimerization domain.

Sequence identity: The similarity between amino acid sequences or nucleic acid sequences is expressed in terms of the similarity and/or identity between the sequences. Sequence similarity may include elements of sequence identity and sequences that are closely related by homology. Sequence similarity is frequently measured in terms of percentage similarity (or identity or homology); the higher the percentage, the more similar the two sequences are. Homologs or variants of a given gene or protein will possess a relatively high degree of sequence identity when aligned using standard methods. Methods of alignment of sequences for comparison are well known in the art. Various programs and alignment algorithms are described in the art: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genet. 6:119-129, 1994. The NCBI Basic Local Alignment Search Tool (BLAST®) (Altschul et al., J. Mol. Biol. 215:403-410, 1990) is available from several sources, including the National Center for Biotechnology Information (NCBI, Bethesda, Md.) for use in connection with the sequence analysis programs blastp, blastn, blastx, tblastn and tblastx.

Subject: As used herein, refers to any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In certain embodiments, the non-human subject is a mammal (e.g., a rodent, a mouse, a rat, a rabbit, a monkey, a dog, a cat, a sheep, cattle, a primate, and/or a pig). In some embodiments, a subject may be a transgenic animal, genetically-engineered animal, and/or a clone. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Vaccination: As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, an influenza VLP as described herein comprises HA polypeptides and/or NA polypeptides. In some embodiments, an influenza VLP as described herein comprises HA polypeptides, NA polypeptides and/or structural polypeptides. In some certain embodiments, an influenza VLP as described herein comprises HA polypeptides, NA polypeptides and/or influenza M1 polypeptides. In some embodiments, an influenza VLP as described herein comprises HA polypeptides, NA polypeptides and/or HIVgag polypeptides. Persons skilled in the art are aware that other viral structural proteins may be used as alternatives to those exemplified herein. Influenza VLPs can be produced by transfection of host cells (e.g., mammalian cells) with plasmids encoding HA and NA proteins, and optionally M1 proteins and/or HIV gag proteins. After incubation of the transfected cells for an appropriate time to allow for protein expression, VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. For example, influenza VLP particle size may be analyzed by dynamic light scattering, and such VLPs may also be analyzed for hemagglutinin activity, and hemagglutinin content quantitation by protein staining.

Wild type: As is understood in the art, the term "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database.

Methods for Designing Hemagglutinin (HA) Polypeptides

A significant challenge associated with generating a consensus influenza protein sequence relates to temporal and geographic sequence biases. Such biases exist in part because the sequence records provided in public and/or private sequence databases are often heavily skewed to more recent sequences. Further, sequences associated with certain geographical regions such as the United States are often over-represented. In one aspect, the present invention provides novel methods for generating influenza HA polypeptides comprising consensus amino acids using a cluster-based consensus approach that overcomes such temporal and geographic sequence biases. The methods of the invention are independent of phylogenetic information and dependent only upon the information contained in primary amino acid sequences. Accordingly, the present methods are able to generate HA polypeptide sequences that reflect overall sequence diversity and not biased towards temporally or geographically over-represented sequences.

In various embodiments, the methods involve designing HA polypeptide sequences based on in silico analysis of the sequence variations among multiple influenza HA sequences, applying a consensus-based sequence algorithm to generate clusters of similar sequences, and conducting structural analysis of HA polypeptides having consensus amino acid sequences. In some embodiments, the present methods generate pairwise similarity/dissimilarity matrices that could be clustered using tools such as K-means, Minimax clustering, and Farthest-First clustering. Alternatively or additionally, the pairwise similarity/dissimilarity matrices are visualized in a compact representation using ordination techniques such as Multidimensional Scaling (MDS) or Principal Components Analysis (PCA) so as to define appropriate clusters (e.g., to separate and define the number of clusters). Further still, the present methods utilize molecular modeling and comparisons to crystal structures to resolve variable amino acid positions within the consensus sequences and to rank candidates that are likely to fold properly and thus be functional.

Without wishing to be bound by theory, it is believed that methods of the invention generate HA polypeptides comprising conserved epitopes across different influenza strains, types, and/or subtypes. Accordingly, in various embodiments, the present methods generate HA polypeptides capable of inducing an enhanced cross-reactive immune response against a broad range of influenza strains (e.g., one or more seasonal, pandemic, or swine strains), influenza types (e.g., one or more influenza type A, type B, or type C), and/or influenza subtypes (e.g., one or more influenza subtypes such as, without limitation, H1N1, H3N2, or H5N1).

In some embodiments, the present methods comprise selecting various influenza HA polypeptide sequences. A variety of different HA sequences can be found in sequence databases, such as the National Center for Biotechnology Information (NCBI) influenza virus sequence database. In some embodiments, a non-redundant subset of unique sequences is selected for sequence alignment.

In some embodiments, the present methods comprise aligning the influenza HA polypeptide sequences. Any multiple sequence alignment tool known in the art may be used. See, for example, Katoh and Kuma (2002) NAR, 30:3059; Katoh and Standley (2013) Mol BioL Evol 30:772; Edgar, R. C. (2004) NAR, 32:1792; Edgar, R. C. (2004) BMC Bioinf, 113; Sievers et al. (2011) Mol Sys Biol 7:539; and Pearson and Lipman. (1988) PNAS, 85:2444). Exemplary sequence alignment tools that may be utilized for the present invention include, but are not limited to, MAFFT, MUSCLE, CLUSTAL OMEGA, FASTA, or a combination thereof.

In some embodiments, specific sequence regions may be masked from further analysis. For example, any one of HA signal peptide sequences, transmembrane domain sequences, cytoplasmic tail sequences, or any other conserved HA domains may be masked from further analysis.

In some embodiments, the present methods comprise calculating pairwise similarity/dissimilarity matrices from the aligned sequences. Any methods for calculating the distances between two or more sequences may be used. Exemplary tools for calculating pairwise similarity/dissimilarity matrices include, but are not limited to, BLOSUM, PAM, IDENTITY substitution matrices, or a combination thereof. In an embodiment, an alternative method for calculating pairwise similarity/dissimilarity matrices such as FastTree may be used (Price, M. N., Dehal, P. S., and Arkin, A. P. (2009) Molecular Biology and Evolution 26:1641-1650).

In some embodiments, the present methods further comprise identifying and creating clusters of similar sequences from the pairwise similarity/dissimilarity matrices. Exemplary tools for identifying the clusters of similar sequences include, but are not limited to, K-means clustering, minimax clustering, Farthest-First clustering, principle component analysis (PCA), multidimensional scaling (MDS), or a combination thereof. In an embodiment, the K-means methods for clustering is utilized (see Hartigan, J. A. et al. (1979) Journal of the Royal Statistical Society, Series C, Applied Statistics, 28(1): 100-108). In another embodiment, minimax clustering (e.g., minimax linkage hierarchical clustering of similarity matrix) is utilized (see, Bien, J. et al., (2011) The Journal of the American Statistical Association). In a further embodiment, farthest-first traversal is used (see Rosenkrantz et al. (1977) SIAM J Comp, 6: 563).

In some embodiments, ordination techniques may be used for identifying and creating clusters of similar sequences from the pairwise similarity/dissimilarity matrices. For example, in some embodiments, PCA is used for dimension reduction of the pairwise similarity/dissimilarity matrix. PCA can be utilized to transform a high dimensional, pairwise similarity/dissimilarity matrix into a lower dimensional subspace to facilitate visualization and identification of clusters of similar sequences (see Pearson, K. (1901) Philosophical Magazine 2(11): 559-572; and Hotelling, H. (1933) Journal of Educational Psychology, 24, 417-441, and 498-520). In a further embodiment, multidimensional scaling (MDS) is used. MDS refers to a means of calculating and visualizing the level of similarity and dissimilarity of multidimensional datasets and finding a reduced set of dimensions that best reproduce the distances between all pairs of a set of points. In some embodiments, MDS is used to place each object in N-dimensional space such that the between-object distances are preserved. In some embodiments, MDS allows display of information contained in a distance matrix. In some embodiments, MDS places the HA sequences in a reduced dimensional space thereby accurately maintaining the relative distances between pairs of viral sequences. In some embodiments, MDS overcomes shortcomings in phylogenetic methods, as phylogenetic methods may be inconsistent in the presence of reassortment and/or recombination. In some embodiments, MDS filters out neutral substitutions in influenza virus that are random. In various embodiments, ordination techniques such as MDS or PCA help to transform the high dimensional, pairwise distance matrix into lower dimensional subspace to facilitate visualization and identification of clusters.

In some embodiments, the methods described herein create more than one cluster of similar sequences (for example, seasonal-like, pandemic-like, or swine-like sequences). Exemplary clusters of sequences for use with the methods described herein are presented, but not limited to, those in FIGS. 1A and 1B.

In some embodiments, within each cluster, a consensus sequence is calculated based on the most frequent amino acid at each position in the multiple sequence alignment. For example, if the frequency of an amino acid at a given position is 50% or greater (or any other user defined threshold), that amino acid is designated a consensus amino acid. Alternatively, if the frequency of an amino acid at a given position is less than 50% (or any other user defined threshold), that amino acid is designated as a variable amino acid. In some embodiments, a first sequence is generated for each cluster which comprises consensus amino acids and variable amino acids. In some embodiments, the first sequence generated for each cluster is designated as a within-cluster consensus sequence.

In some embodiments, a consensus sequence is generated for multiple sequence clusters. In such embodiments, selected within-cluster consensus sequences for multiple clusters are merged based on specified outcome properties so as to derive additional consensus sequences. For example, within-cluster consensus sequences associated with specific geographical regions, hosts, or time periods can be merged to generate an across-cluster consensus sequence (e.g., a second sequence).

In various embodiments, in order to generate across-cluster consensus sequences, a within-cluster consensus sequence (e.g., a first sequence) generated from one cluster is compared with a within-cluster consensus sequence (e.g., a first sequence) generated from another cluster or multiple clusters. In some embodiments, the generated sequences are aligned against one another. In some embodiments, a pairwise alignment method is utilized to determine whether there is a consensus amino acid for each position in the alignment. As described previously, if the frequency of an amino acid at a given position is 50% or greater (or any other user defined threshold), that amino acid is designated a consensus amino acid, and if the frequency of an amino acid at a given position is less than 50% (or any other user defined threshold), that amino acid is designated as a variable amino acid. In some embodiments, an across-cluster consensus sequence (e.g., a second sequence) comprising consensus amino acids and variable amino acids is generated from such multi-cluster analysis. In various embodiments, the process of aligning sequences, and determining consensus amino acids at each position can be performed iteratively until all the sequence clusters of interest are considered.

In some embodiments, an additional step is performed to determine a consensus amino acid for each variable amino acid position within a within-cluster consensus sequence and/or an across-cluster consensus sequence (e.g., the first sequence and/or the second sequence) generated. In such embodiments, a set of test sequences are generated based on the consensus sequences (e.g., a first and/or a second sequence), wherein test amino acids are placed at the variable amino acid positions. The test amino acids used in the methods described herein encompass any natural or non-natural (e.g., non-classical) amino acid found in proteins, including essential and non-essential amino acids. Exemplary amino acids include the amino acids provided in the Table 2 below as well as those described elsewhere herein.

TABLE 2

| Essential | Non-Essential |
| --- | --- |
| Histidine (H) | Alanine (A) |
| Isoleucine (I) | Arginine (R) |
| Leucine (L) | Aspartic acid (D) |
| Lysine (K) | Cysteine (C) |
| Methionine (M) | Glutamic acid (E) |
| Phenylalanine (F) | Glutamine (Q) |
| Threonine (T) | Glycine (G) |
| Tryptophan (W) | Proline (P) |
| Valine (V) | Serine (S) |
| | Tyrosine (Y) |
| | Asparagine (N) |
| | Selenocysteine (U) |
| | Pyrrolysine (O) |

In various embodiments, the present methods contemplate the use of molecular modeling to analyze the test sequences. In some embodiments, molecular modeling is conducted for each of the test sequences. In some embodiments, molecular modeling comprises a comparison to a crystal structure of the influenza protein (i.e., HA) being analyzed. Such crystal structure information is readily available from, for example, the Protein Data Bank. In an embodiment, the molecular modeling comprises use of Rosetta (https://www.rosettacommons.org/software) or any other similar molecular modeling softwares (see, for example, Leaver-Fay et al. (2011) *Meth. Enzymol.* 487:545-74). For example, to resolve variable amino acid positions in the consensus sequences, a Metropolis-Monte Carlo simulated annealing protocol within Rosetta can be used to sample substitutions of all possible combinations of amino acid residues present at the identified sites of variation. Possible substitutions are then scored based on energy value.

In some embodiments, a consensus amino acid for each variable amino acid position is determined by selecting amino acid(s) that result in an HA polypeptide having a calculated total energy value similar to, or below a starting value. In some embodiments, a consensus amino acid for each variable amino acid position is determined by selecting amino acid(s) that result in an HA polypeptide having a negative total energy value. Without wishing to be bound by theory, it is believed that HA polypeptides with negative total energy scores are more likely to fold into stable proteins while polypeptides with positive energy scores are less likely to fold properly. In some embodiments, one or more HA polypeptides are generated and ranked according to their negative total energy scores and/or comparisons to a reference structure.

In various embodiments, the present methods generate an HA polypeptide sequence comprising consensus amino acids at various positions. Exemplary HA polypeptides generated using methods of the invention are provided in Table 1 (i.e., SEQ ID NOs: 1-16).

Hemagglutinin (HA) Polypeptides and Proteins

In another aspect, the present invention provides HA polypeptides generated using the methods described herein. In some embodiments, the HA polypeptides comprise consensus amino acid sequences and are capable of eliciting an immune response against multiple influenza strains (e.g., one or more pandemic, seasonal, and/or swine influenza strains), types (e.g., one or more influenza Type A, Type B, and/or Type C viruses), and/or subtypes (e.g., one or more of H1N1, H3N2, or H5N1). Thus, in some embodiments, the HA polypeptides can be incorporated in vaccine compositions as antigens to provide improved protective immunity against influenza.

In some embodiments, the present invention provides a HA polypeptide comprising an amino acid sequence selected from any one of SEQ ID NOs: 1-16, or a fragment thereof. In some embodiments, the HA polypeptide comprises an amino acid sequence having at least about 80%, 85%, 90%, 95%, 96%, 97%, 98%, or 99% sequence identity to any one of SEQ ID NOs: 1-16, or a fragment thereof.

For example, in some embodiments, the present invention provides an HA polypeptide comprising a fragment of any one of SEQ ID NOs: 1-16. In exemplary embodiments, the HA polypeptide may lack the signal peptide. In another exemplary embodiment, the HA polypeptide may lack a transmembrane domain.

In some embodiments, the present invention provides an HA polypeptide having one or more amino acid mutations relative to any one of SEQ ID NOs: 1-16, or a fragment thereof. For example, the HA polypeptide may comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 amino acid mutations relative to any one of any one of SEQ ID NOs: 1-16, or a fragment thereof.

In some embodiments, the one or more amino acid mutations may be independently selected from substitutions, insertions, deletions, and truncations. In some embodiments, the amino acid mutations are amino acid substitutions, and may include conservative and/or non-conservative substitutions. In some embodiments, the amino acid mutations are amino acid substitutions, and may include conservative and/or non-conservative substitutions.

Conservative substitutions may be made, for instance, on the basis of similarity in polarity, charge, size, solubility, hydrophobicity, hydrophilicity, and/or the amphipathic nature of the amino acid residues involved. For example, the 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. As used herein, "conservative substitutions" are defined as exchanges of an amino acid by another amino acid listed within the same group of the six standard amino acid groups shown above. For example, the exchange of Asp by Glu retains one negative charge in the modified polypeptide. In addition, glycine and proline may be substituted for one another based on their ability to disrupt α-helices. As used herein, "non-conservative substitutions" are defined as exchanges of an amino acid by another amino acid listed in a different group of the six standard amino acid groups shown above.

In various embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In various embodiments, the present invention further provides a trimeric HA protein comprising three HA polypeptides. In some embodiments, at least 1, at least 2, or all 3 HA polypeptides within the trimeric HA protein comprise an amino acid sequence as described herein. For example, at least 1, at least 2, or all 3 HA polypeptides of the trimeric HA protein may comprise the amino acid sequence of SEQ ID NOs: 1-16, or a fragment thereof. In some embodiments, the trimeric HA protein comprises three identical HA polypeptides. In other embodiments, the trimeric HA protein comprises two or more non-identical HA polypeptides having distinct amino acid sequences.

In various embodiments, the present invention further provides a fusion protein comprising the HA polypeptide of the invention, or a fragment thereof.

In various embodiments, the HA polypeptides of the invention may comprise a trimerization sequence or a trimerization domain which promotes assembly of monomeric HA polypeptides into a trimeric HA protein. In some embodiments, the HA polypeptides may comprise sequences or domains that promote trimerization that are present in HA polypeptides found in natural influenza isolates. For example, the HA polypeptides may comprise sequences found in the HA2 sequence comprising the stem region, which are known to promote trimer formation. In other embodiments, the HA polypeptides may comprise an engineered or a heterologous trimerization sequence or trimerization domain that is not naturally present in wild type HA polypeptides. In various embodiments, the HA polypeptides may be engineered to comprise any trimerization sequence or trimerization domain. Exemplary trimerization sequences include but are not limited to, amino acids that form either covalent or non-covalent cross-links, and trimerization domains include, but are not limited to, the trimerization domain of collagen, a GCN4-based isoleucine zipper, an HIV gp41 trimerization domain, or the T4 bacteriophage fibritin foldon (Fd) trimerization domain.

In some embodiments, the HA polypeptides may comprise a secretion signal peptide. In an embodiment, the incorporation of the secretion signal peptide allows for the HA polypeptide or the trimeric HA protein to be secreted from host cells. In another embodiment, the incorporation of the secretion signal peptide allows for purification of the HA polypeptide or the trimeric HA protein from host cells (e.g., the supernatant of host cells) used for protein expression and production.

It is contemplated that any secretion signal peptide known in the art may be incorporated into the HA polypeptides of the invention. In some embodiments, the secretion signal peptide is specific for the host cell used for protein expression and production. Exemplary secretion signal peptides include, but are not limited to, the CD33 signal peptide sequence, the human IgG Kappa light chain signal peptide (for expression in human cells), the honey bee melittin signal sequence (for expression in insect cells) and the yeast alpha-factor signal sequence (for expression in yeast cells). In an exemplary embodiment, the secretion signal sequence is a CD5 secretion signal peptide. In an embodiment, the CD5 secretion signal peptide comprises the amino acid sequence of SEQ ID NO: 17.

In some embodiments, the HA polypeptide comprises additional functional sequences such as a linker sequence. In some embodiments, the linker is a polypeptide. In some embodiments, the linker is less than about 100 amino acids long. For example, the linker may be less than about 100, about 90, about 80, about 70, about 60, about 50, about 40, about 30, about 20, about 19, about 18, about 17, about 16, about 15, about 14, about 13, about 12, about 11, about 10, about 9, about 8, about 7, about 6, about 5, about 4, about 3, or about 2 amino acids long.

In various embodiments, the linker is substantially comprised of glycine and/or serine residues (e.g., about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g., 1, 2, 3, 4, 5, 6, 7, or 8 (SEQ ID NO: 19). In an embodiment, the linker sequence is GGSGGSGGGGSGGGGS (SEQ ID NO: 20). Additional illustrative linkers include, but are not limited to, linkers having the sequence LE, GGGGS (SEQ ID NO: 21), $(GGGGS)_n$ (n=1-4) (SEQ ID NO: 22), $(Gly)_8$ (SEQ ID NO: 23), $(Gly)_6$ (SEQ ID NO: 24), $(EAAAK)_n$ (n=1-3) (SEQ ID NO: 25), $A(EAAAK)_nA$ (n=2-5) (SEQ ID NO: 26), AEAAAKEAAAKA (SEQ ID NO: 27), $A(EAAAK)_4ALEA(EAAAK)_4A$ (SEQ ID NO: 28), PAPAP (SEQ ID NO: 29), KESGSVSSEQLAQFRSLD (SEQ ID NO: 30), EGKSSGSGSESKST (SEQ ID NO: 31), GSAGSAAGSGEF (SEQ ID NO: 32), and $(XP)_n$, with X designating any amino acid, e.g., Ala, Lys, or Glu. In an exemplary embodiment, the linker is GGS or GSG. In another exemplary embodiment, the linker is SA.

In some embodiments, the HA polypeptide further comprises a functional tag sequence (for example, to facilitate protein purification). Without limitation, the HA polypeptide may comprise affinity tags such as glutathione-S-transferase (GST), polyhistidine (e.g., 6xHis (SEQ ID NO: 33)), protein A, Streptavidin/Biotin-based tags, as well as any other protein tags known in the art.

In some embodiments, the HA polypeptide further comprises a protease cleavage site such as a thrombin cleavage site, a trypsin cleavage site, an enterokinase cleavage site, or any other protease cleavage sites known in the art.

In various embodiments, the HA polypeptides (or trimeric HA proteins) described herein provide for improved protective immunity (e.g., a broadly reactive immune response) against a range of influenza viruses with divergent sequences. In various embodiments, the HA polypeptides (or the trimeric HA proteins) described herein elicit an enhanced immune response against conserved epitopes among multiple influenza strains. In various embodiments, the HA polypeptides (or the trimeric HA proteins) described herein induce immune responses against different influenza viruses exhibiting antigenic shift or antigenic drift.

In some embodiments, the HA polypeptides or the trimeric HA proteins described herein exhibit greater immunogenicity across different influenza strains/types/subtypes as compared to an HA polypeptide or a trimeric HA protein from wildtype or naturally-occurring influenza virus strains. In some embodiments, the HA polypeptides or the trimeric HA proteins described herein have greater stability compared to an HA polypeptide or a trimeric HA protein from wildtype or naturally-occurring influenza virus strains.

Nucleic Acid Construction and Expression

In various embodiments, a method of producing recombinant HA polypeptides is provided. The method comprises generating an HA polypeptide comprising a consensus amino acid sequence using the cluster-based consensus method described herein, and producing the HA polypeptide by transfecting a host cell with a vector encoding the HA polypeptide. In various embodiments, methods for producing recombinant trimeric HA proteins are also provided.

In some embodiments, the HA polypeptides as described herein may be produced from nucleic acids using molecular biology methods known in the art. For example, nucleic acid molecules are inserted into a vector that is able to express the HA polypeptides when introduced into an appropriate host cell. Appropriate host cells include, but are not limited to, bacterial, yeast, insect, and mammalian cells, as well as any other cell types described elsewhere herein. Any of the methods known to one skilled in the art for the insertion of DNA fragments into a vector may be used to construct expression vectors encoding the HA polypeptides under control of transcriptional/translational control signals. These methods may include in vitro recombinant DNA and synthetic cloning techniques and in vivo recombination techniques (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, N.Y.).

In some embodiments, the present invention provides nucleic acids which encode an HA polypeptide or a characteristic or biologically active portion of an HA polypeptide. In some embodiments, the invention provides nucleic acids which are complementary to nucleic acids which encode an HA polypeptide or a characteristic or biologically active portion of an HA polypeptide. In other embodiments, the present invention further provides nucleic acids which encode a trimeric HA protein.

In some embodiments, the invention provides nucleic acid molecules which hybridize to nucleic acids encoding an HA polypeptide or a characteristic or biologically active portion of an HA polypeptide. Such nucleic acids can be used, for example, as primers or as probes. In exemplary embodiments, such nucleic acids can be used as primers in polymerase chain reaction (PCR), as probes for hybridization (including in situ hybridization), and/or as primers for reverse transcription-PCR (RT-PCR).

In some embodiments, nucleic acids can be DNA or RNA, and can be single stranded or double-stranded. In some embodiments, nucleic acids in accordance with the invention may include one or more non-natural nucleotides. In some embodiments, nucleic acids in accordance with the invention include only natural nucleotides.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element known in the art.

In some embodiments, an expression vector containing a nucleic acid molecule is transformed into a suitable host cell to allow for production of the HA polypeptides or proteins encoded by the nucleic acid constructs. Host cells transformed with an expression vector are then grown under conditions permitting production of an HA polypeptide or a trimeric HA protein of the present invention followed by recovery of the polypeptide or protein. Exemplary cell types that may be used in the present invention include, but are not limited to, mammalian cells, insect cells, yeast cells, plant cells, and bacterial cells. Insect cells include, but are not limited to: SF cells, caterpillar cells, butterfly cells, moth cells, SF9 cells, SF21 cells, drosophila cells, S2 cells, fall armyworm cells, cabbage looper cells, Spodoptera frugiperda cells, and Trichoplasia ni cells. Suitable mammalian cells include, but are not limited to: Madin-Darby canine kidney (MDCK) cells, VERO cells, EBx cells, chicken embryo cells, Chinese hamster ovary (CHO) cells, monkey kidney cells, human embryonic kidney cells, HEK293T cells, NS0 cells, myeloma cells, hybridoma cells, primary adenoid cell lines, primary bronchial epithelium cells, transformed human cell lines, and Per.C6 cells. Other useful cells or cellular systems include, but are not limited to, plant-based systems (e.g., tobacco plants; see, e.g., Jul-Larsen, A., et al., Hum Vaccin Immunother., 8(5):653-61, 2012), yeast (see, e.g., Athmaram, T. N. et al., Virol J., 8:524, 2011), and fungi (see, e.g., Allgaier, S. et al., Biologicals, 37:128-32, 2009). Bacterial based expression systems are also encompassed by the present invention (see, e.g., Davis, A. R. et al., Gene, 21:273-284, 1983). The present invention further contemplates the use of a baculovirus system.

The HA polypeptides or trimeric HA proteins of the present invention may be purified by any technique known in the art. For example, the HA polypeptides or trimeric HA proteins may be recovered from cells either in soluble fractions or as inclusion bodies, from which they may be extracted by, for example, guanidinium hydrochloride and dialysis. In order to further purify the HA polypeptides or trimeric HA proteins, conventional ion exchange chromatography, hydrophobic interaction chromatography, reverse phase chromatography, size exclusion chromatography, affinity chromatography, gel filtration, or combinations thereof, may be used. In some embodiments, the HA polypeptides or trimeric HA proteins may also be recovered from conditioned media following secretion from eukaryotic or prokaryotic cells. In such embodiments, a purified recombinant HA polypeptide or trimeric HA protein is produced by culturing the host cell under conditions sufficient for the cell to secrete the polypeptide or protein into the culture supernatant and purifying the polypeptide or protein from the supernatant.

In some embodiments, the recombinant HA polypeptide is purified from a host cell as a monomer. In other embodiments, the recombinant HA polypeptide is purified from a host cell as a trimer.

Evaluation of HA Polypeptides and Proteins

In some embodiments, the present invention contemplates evaluating the HA polypeptides or trimeric HA proteins produced using the methods described herein to determine whether it (i) elicits an immune response to one or more influenza viruses; (ii) provides a protective immune response against one or more influenza viruses, or (iii) produces antibodies directed against one or more influenza viruses after administration to a subject. Various methods for testing such functions are well known in the art, and may be utilized.

In some embodiments, the HA polypeptides or trimeric HA proteins generated according to methods described herein are assessed for desired expression and conformation. Screening methods are well known to the art and include cell-free, cell-based, and animal assays. In vitro assays include solid state or soluble target molecule detection methods involving the use of detectable labels. In such assays, the HA polypeptides or trimeric HA proteins may be identified through binding to a target molecule (e.g., an immunoglobulin). In some embodiments, the HA polypeptides or proteins as described herein may be selected based on desired expression and conformational characteristics.

The present invention further provides methods for testing HA polypeptides in an animal host. As used herein, an "animal host" includes any animal model suitable for influenza research. For example, animal hosts include mammalian hosts including, but not limited to, primates, ferrets, cats, dogs, cows, horses, rabbits, and rodents such as, mice, hamsters, and rats. In some embodiments, the animal host is inoculated with, infected with, or otherwise exposed to influenza virus prior to or concurrent with administration of an HA polypeptide or a trimeric HA protein. Alternatively, the animal host may be administered with a DNA molecule encoding the HA polypeptide or trimeric HA protein. An animal host can be inoculated with, infected with, or otherwise exposed to influenza virus by any method known in the art including through intranasal routes.

In some embodiments, an animal host is naive to viral exposure or infection prior to administration of the HA polypeptide or trimeric HA protein (optionally, as a component in a composition). Naive and/or inoculated animals may be used for any of a variety of studies. For example, such animal models may be used for virus transmission studies as in known in the art. For example, air transmission of viral influenza from inoculated animals (e.g., ferrets) to naive animals is known (Tumpey et al., 2007, Science 315; 655-59). In an exemplary viral transmission study, HA polypeptides or trimeric HA proteins may be administered to a suitable animal host in order to determine the efficacy of said HA polypeptides or proteins in eliciting a broad immune response in the animal host. Using such information gathered from studies in an animal host, one may predict the efficacy of an HA polypeptide or protein to elicit an immune response in a human host.

Influenza Virus-Like Particles (VLPs)

In some embodiments, the present invention provides for influenza virus-like particles (VLPs) comprising the HA polypeptide or the trimeric HA protein as described herein. The influenza VLPs are, in some embodiments, generally made up of HA, NA and/or virus structural proteins (e.g., HIV gag, influenza M1 proteins). Production of influenza VLPs is known in the art. For example, influenza VLPs may be produced by transfection of host cells with plasmids encoding the HA, NA and/or HIV gag or M1 proteins. In exemplary embodiments, a suitable host cell includes a human cell (e.g., HEK293T). After incubation of the transfected cells for an appropriate time to allow for protein expression (e.g., approximately 72 hours), VLPs may be isolated from cell culture supernatants. In some embodiments, influenza VLPs as disclosed herein may be used as influenza vaccines to elicit a broadly neutralizing immune response against one or more influenza viruses.

Pharmaceutical Compositions and Administration

In various embodiments, the present invention provides for pharmaceutical compositions comprising the HA polypeptide or the trimeric HA protein as described herein and/or related entities. In some embodiments, the pharmaceutical composition is an immunogenic composition (e.g., a vaccine) capable of eliciting an immune response such as a protective immune response against the influenza virus.

For example, in some embodiments, the pharmaceutical compositions may comprise one or more of the following: (1) live attenuated influenza virus, for example, replication-defective virus, (2) inactivated virus, (3) virus-like particles (VLPs), (4) recombinant HA polypeptide or recombinant trimeric HA protein of the invention, or characteristic or biologically active portion thereof, (5) nucleic acid encoding the HA polypeptide or the trimeric HA protein of the invention, or characteristic or biologically active portion thereof, (6) DNA vector that encodes the HA polypeptide or the trimeric HA protein of the invention, or characteristic or biologically active portion thereof, and/or (7) an expression system, for example, cells expressing the HA polypeptide or the trimeric HA protein of the invention.

In some embodiments, the present invention provides pharmaceutical compositions comprising antibodies or other agents related to the HA polypeptides or the trimeric HA proteins of the invention. In an embodiment, the pharmaceutical composition comprises antibodies that bind to and/or compete with the HA polypeptides or trimeric HA proteins described herein. Alternatively, the antibodies may recognize viral particles comprising the HA polypeptides or trimeric HA proteins described herein. In another embodiment, the pharmaceutical composition comprises small molecules that interact with or compete with the HA polypeptides or trimeric HA proteins described herein. In a further embodiment, the pharmaceutical composition comprises nucleic acids, such as nucleic acids having sequences complementary to the HA polypeptide sequences, which can be used for gene silencing.

In some embodiments, the pharmaceutical compositions as described herein are administered alone or in combination with one or more agents to enhance an immune response. For example, in some embodiments, the pharmaceutical compositions are administered in combination with an adjuvant. The present invention contemplates the use of any known adjuvants. Exemplary adjuvants include, but are not limited to, Freund incomplete adjuvant or Freund's complete adjuvant. In some embodiments, one or more cytokines (e.g., IL-2, IL-6, IL-12, RANTES, GM-CSF, TNF-α, or IFN-γ), one or more growth factors (e.g., GM-CSF or G-CSF), one or more molecules such as OX-40L or 41 BBL, or a combination thereof, may be used as biological adjuvants. In some embodiments, the pharmaceutical compositions may include aluminum salts and monophosphoryl lipid A as adjuvants. Alternatively, or additionally, adjuvants utilized in human vaccines, such as MF59 (Chiron Corp.), CPG 7909 (Cooper et al., (2004) Vaccine, 22:3136), and saponins, such as QS21 (Ghochikyan et al., (2006) Vaccine, 24:2275) may be used. Further examples of adjuvants include, but are not limited to, poly[di(carboxylatophenoxy) phosphazene] (PCCP; Payne et al., (1998) Vaccine, 16:92), the block copolymer P1205 (CRL1005; Katz et al., (2000) Vaccine, 18:2177), and polymethyl methacrylate (PMMA; Kreuter et al., (1981) J. Pharm. Sci., 70:367). Additional adjuvants are described elsewhere herein.

In some embodiments, the pharmaceutical composition further comprises a pharmaceutically acceptable carrier or excipient. As used herein, the term "carrier" refers to a diluent, adjuvant, excipient, or vehicle with which a pharmaceutical composition is administered. In exemplary embodiments, carriers can include sterile liquids, such as, for example, water and oils, including oils of petroleum, animal, vegetable, or synthetic origin, such as, for example, peanut oil, soybean oil, mineral oil, sesame oil and the like. In some embodiments, carriers are or include one or more solid components. Pharmaceutically acceptable carriers can also include, but are not limited to, saline, buffered saline, dextrose, glycerol, ethanol, and combinations thereof. As used herein, an excipient is any non-therapeutic agent that may be included in a pharmaceutical composition, for example to provide or contribute to a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In various embodiments, the pharmaceutical composition is sterile.

In some embodiments, the pharmaceutical composition contains minor amounts of wetting or emulsifying agents, or pH buffering agents. In some embodiments, the pharmaceutical compositions of may include any of a variety of additives, such as stabilizers, buffers, or preservatives. In addition, auxiliary, stabilizing, thickening, lubricating, and coloring agents can be included.

In various embodiments, the pharmaceutical composition may be formulated to suit any desired mode of administration. For example, the pharmaceutical composition can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, dessicated powder, or any other form suitable for use. General considerations in the formulation and manufacture of pharmaceutical agents may be found, for example, in *Remington's Pharmaceutical Sciences*, 19$^{th}$ ed., Mack Publishing Co., Easton, Pa., 1995; incorporated herein by reference.

The pharmaceutical composition can be administered via any route of administration. Routes of administration include, for example, oral, intradermal, intramuscular, intraperitoneal, intravenous, subcutaneous, intranasal, mucosal, epidural, sublingual, intranasal, intracerebral, intravaginal, transdermal, rectally, by intratracheal instillation, bronchial instillation, inhalation, or topically. Administration can be local or systemic. In some embodiments, administration is carried out orally. In another embodiment, the administration is by parenteral injection. In some instances, administration results in the release of the HA polypeptide or trimeric HA protein described herein into the bloodstream. The mode of administration can be left to the discretion of the practitioner.

In an embodiment, the pharmaceutical composition is adapted for oral administration. Compositions for oral delivery can be in the form of tablets, lozenges, aqueous or oily suspensions, granules, powders, emulsions, capsules, syrups, or elixirs, for example.

In another embodiment, the pharmaceutical composition is suitable for parenteral administration (e.g., intravenous, intramuscular, intraperitoneal, and subcutaneous). Such compositions can be formulated as, for example, solutions, suspensions, dispersions, emulsions, and the like. They may also be manufactured in the form of sterile solid compositions (e.g., lyophilized composition), which can be dissolved or suspended in sterile injectable medium immediately before use. For example, parenteral administration can be achieved by injection. In such embodiments, injectables are prepared in conventional forms, i.e., either as liquid solutions or suspensions, solid forms suitable for solution or suspension in liquid prior to injection, or as emulsions. In some embodiments, injection solutions and suspensions are prepared from sterile powders, lyophilized powders, or granules.

In a further embodiment, the pharmaceutical composition is formulated for delivery by inhalation (e.g., for direct delivery to the lungs and the respiratory system). For example, the composition may take the form of a nasal spray or any other known aerosol formulation. In some embodiments, preparations for inhaled or aerosol delivery comprise a plurality of particles. In some embodiments, such preparations can have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, the pharmaceutical composition in accordance with the invention are administered as drops to the nasal or buccal cavity. In some embodiments, a dose may comprise a plurality of drops (e.g., 1-100, 1-50, 1-20, 1-10, 1-5, etc.).

In some embodiments, the pharmaceutical composition will include an HA polypeptide or a trimeric HA protein that is encapsulated, trapped, or bound within a lipid vesicle, a bioavailable and/or biocompatible and/or biodegradable matrix, or other microparticles. In some embodiments, the pharmaceutical composition comprises nanoparticles displaying the HA polypeptides or trimeric HA proteins. In some embodiments, the nanoparticles are ferritin nanoparticles (see, e.g., U.S. patent publication 2014/0072958).

The present pharmaceutical composition may be administered in any dose appropriate to achieve a desired outcome. In some embodiments, the desired outcome is the induction of a long-lasting adaptive immune response against one or more influenza strains. In some embodiments, the desired outcome is a reduction in the intensity, severity, frequency, and/or delay of onset of one or more symptoms of influenza infection. In some embodiments, the desired outcome is the inhibition or prevention of influenza virus infection. The dose required will vary from subject to subject depending on the species, age, weight, and general condition of the subject, the severity of the infection being prevented or treated, the particular composition being used, and its mode of administration.

In some embodiments, pharmaceutical compositions in accordance with the invention are administered in single or multiple doses. In some embodiments, the pharmaceutical compositions are administered in multiple doses administered on different days (e.g., prime-boost vaccination strategies). In some embodiments, the pharmaceutical compositions are administered according to a continuous dosing regimen, such that the subject does not undergo periods of less than therapeutic dosing interposed between periods of therapeutic dosing. In some embodiments, the pharmaceutical compositions are administered according to an intermittent dosing regimen, such that the subject undergoes at least one period of less than therapeutic dosing interposed between two periods of therapeutic dosing. In some embodiments, the pharmaceutical composition is administered as part of a booster regimen.

In various embodiments, the pharmaceutical composition is co-administered with one or more additional therapeutic agents. Co-administration does not require the therapeutic agents to be administered simultaneously, if the timing of their administration is such that the pharmacological activities of the additional therapeutic agent and the HA polypeptide or the trimeric HA protein overlap in time, thereby exerting a combined therapeutic effect. In general, each agent will be administered at a dose and on a time schedule determined for that agent.

In some embodiments, the present invention encompasses the delivery of the pharmaceutical composition in combination with agents that may improve their bioavailability, reduce or modify their metabolism, inhibit their excretion, and/or modify their distribution within the body. In some embodiments, the pharmaceutical composition as described herein is administered in combination with one or more of an anti-viral agent (e.g., Oseltamivir [TAMIFLU®] or Zanamavir [RELEZA®], etc.).

Antibodies to HA Polypeptides

The present invention provides antibodies to HA polypeptides or trimeric HA proteins generated in accordance with the invention. These may be monoclonal or polyclonal and may be prepared by any of a variety of techniques known to those of ordinary skill in the art (e.g., see Harlow and Lane, 1988, Antibodies: A Laboratory Manual, Cold Spring Harbor Laboratory; incorporated herein by reference). For example, antibodies can be produced by cell culture techniques, including the generation of monoclonal antibodies, or via transfection of antibody genes into suitable bacterial or mammalian host cells, in order to allow for the production of antibodies.

In some embodiments, the antibodies may be a classic antibody comprised of two heavy chains and two light chains. In other embodiments, the antibody may be an antibody derivative. For example, in some embodiments, the antibody may be a single-domain antibody, a recombinant heavy-chain-only antibody (VHH), a single-chain antibody (scFv), a shark heavy-chain-only antibody (VNAR), a microprotein (cysteine knot protein, knottin), a DARPin, a Tetranectin, an Affibody, a Transbody, an Anticalin, an AdNectin, an Affilin, a Microbody, a peptide aptamer, an alterases, a plastic antibodies, a phylomer, a stradobodies, a maxibodies, an evibody, a fynomer, an armadillo repeat protein, a Kunitz domain, an avimer, an atrimer, a probody, an immunobody, a triomab, a troybody; a pepbody; a vaccibody, a UniBody; affimers, a DuoBody, a Fv, a Fab, a Fab', a F(ab')$_2$, a peptide mimetic molecule, or a synthetic molecule, or any other antibody formats known in the art.

Methods of Immunization and Protection from Influenza Viruses

In another aspect, the present invention provides methods of immunizing a subject against one or more influenza viruses in a subject. The present invention further provides methods of eliciting an immune response against one or more influenza viruses in a subject. In some embodiments, the present methods comprise administering to the subject an effective amount of a pharmaceutical composition described herein to a subject. In some embodiments, the present methods comprise administering to the subject an effective amount of a recombinant HA polypeptide or a trimeric HA protein described herein to a subject. In some embodiments, the present methods comprise administering to the subject an effective amount of a VLP comprising an HA polypeptide or a trimeric HA protein described herein to a subject.

In various embodiments, the methods of immunizing provided herein elicit a broadly protective immune response against multiple epitopes within one or more influenza viruses. In various embodiments, the methods of immunizing provided herein elicit a broadly neutralizing immune response against one or more influenza viruses. In some embodiments, the immune response comprises an antibody response. Accordingly, in various embodiments, the pharmaceutical composition described herein can offer broad cross-protection against different types of influenza viruses. In some embodiments, the pharmaceutical composition offers cross-protection against avian, swine, seasonal, and/or pandemic influenza viruses. In some embodiments, the pharmaceutical composition offers cross-protection against one or more influenza A, B, or C subtypes. In some embodiments, the pharmaceutical composition offers cross-protection against multiple strains of influenza A H1-subtype viruses (e.g., H1N1), influenza A H3-subtype viruses (e.g., H3N2), and/or influenza A H5-subtype viruses (e.g., H5N1).

In some embodiments, the methods of the invention are capable of eliciting an improved immune response against one or more seasonal influenza strains. Exemplary seasonal strains include, without limitation, A/Puerto Rico/8/1934, A/Fort Monmouth/1/1947, A/Chile/1/1983, A/Texas/36/1991, A/Singapore/6/1986, A/Beijing/32/1992, A/New Caledonia/20/1999, A/Solomon Islands/03/2006, and A/Brisbane/59/2007. In some embodiments, the methods of the invention are capable of eliciting an improved immune response against one or more pandemic influenza strains. Exemplary pandemic strains include, without limitation, A/California/07/2009, A/California/04/2009, A/Belgium/145/2009, A/South Carolina/01/1918, and A/New Jersey/1976. Pandemic subtypes include, in particular, the H5N1, H2N2, H9N2, H7N7, H7N3, H7N9 and H10N7 subtypes. In some embodiments, the methods of the invention are capable of eliciting an improved immune response against one or more swine influenza strains. Exemplary swine strains include, without limitation, A/New Jersey/1976 isolates and A/California/07/2009. Additional influenza pandemic, seasonal, and/or swine strains are known in the art.

In various embodiments, the present methods may extend immune protection across a range of antigenically distinct influenza strains. For example, the methods of the invention may elicit an immune response against new pandemic strains arising from antigenic shift (i.e., so that they cover antigenically distinct strains that are distantly separated in genetic sequence space across extended timelines). The present methods can also be applied to address genetic changes that occur over relatively shorter time periods so that the pharmaceutical compositions of the invention continue to be effective by eliciting an immune response against antigenically drifted circulating seasonal strains (e.g., an improved seasonal response). Accordingly, in various embodiments, the present methods may be used: (1) to extend coverage (i.e., capability of eliciting a neutralizing immune response) against one or more seasonal strains; (2) to extend coverage against one or more pandemic strains (to address antigenic drift); and (3) to extend coverage against any other antigenically distinct influenza strains. It is contemplated that the present methods can provide broad, long-lasting (e.g., multi-season) protection against influenza viruses including mismatched strains.

In some embodiments, the present invention provides methods of preventing or treating influenza infections by administering the pharmaceutical compositions of the invention to a subject in need thereof. In some embodiments, the subject is suffering from or susceptible to an influenza infection. In some embodiments, a subject is considered to be suffering from an influenza infection if the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In various embodiments, the pharmaceutical composition as described herein may be administered prior to or after development of one or more symptoms of influenza infection. In some embodiments, the pharmaceutical composition is administered as a prophylactic. In such embodiments, the methods of the invention are effective in preventing or protecting a subject from influenza virus infection. In some embodiments, the pharmaceutical composition of the present invention is used as a component of a seasonal and/or pandemic influenza vaccine or as part of an influenza vaccination regimen intended to confer long-lasting (multi-season) protection. In some embodiments, the pharmaceutical composition of the presenting invention is used to treat the symptoms of influenza infection.

In some embodiments, subjects suffering from or susceptible to influenza infection are tested for antibodies to the HA polypeptides or trimeric HA proteins of the invention prior to, during, or after administration of pharmaceutical compositions in accordance with the invention. In some embodiments, subjects having such antibodies are not administered the pharmaceutical compositions of the invention. In some embodiments, an appropriate dose of a pharmaceutical composition is selected based on detection (or lack thereof) of such antibodies.

In various embodiments, a subject is any member of the animal kingdom. In some embodiments, the subject is a non-human animal. In some embodiments, the subject is a mammal, an avian (e.g., a chicken or a bird), a reptile, an amphibian, a fish, an insect, and/or a worm. In certain embodiments, the non-human subject is a mammal (e.g., a rodent, a mouse, a rat, a rabbit, a monkey, a dog, a cat, a sheep, cattle, a primate, and/or a pig). In some embodiments, a subject is a transgenic animal, genetically-engineered animal, and/or a clone.

In some embodiments, the subject is a human. In certain embodiments, the subject is an adult, an adolescent, or an infant. In some embodiments, the human subject is younger than 6 months of age. In some embodiments, the human subject is 6 months of age or older, is 6 months through 35 months of age, is 36 months through 8 years of age, or 9 years of age or older. In some embodiments, the human subject is an elderly aged 55 years or older, such as 60 year of age or older, or 65 years of age or older. Also contemplated by the present invention are the administration of the pharmaceutical compositions and/or performance of the methods of treatment in-utero.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items The present invention will be more fully understood by reference to the following Examples. All literature citations included herein are incorporated by reference.

EXAMPLES

The following examples are provided to illustrate certain disclosed embodiments and are not to be construed as limiting the scope of this disclosure in any way. As used herein, CBC HA refers to HA polypeptides or proteins designed using the cluster-based consensus (CBC) approach described herein.

Figure 1A:
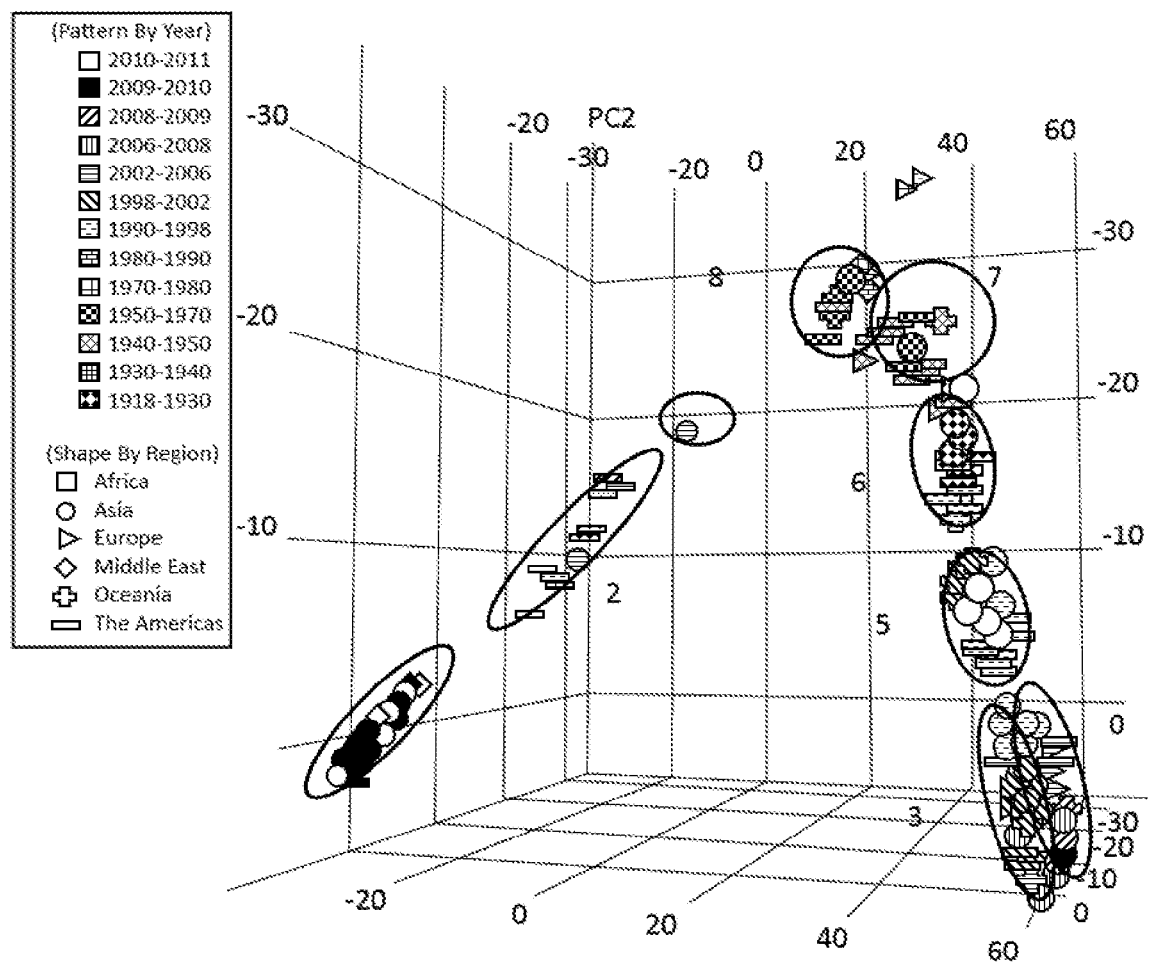
Figure 1B:
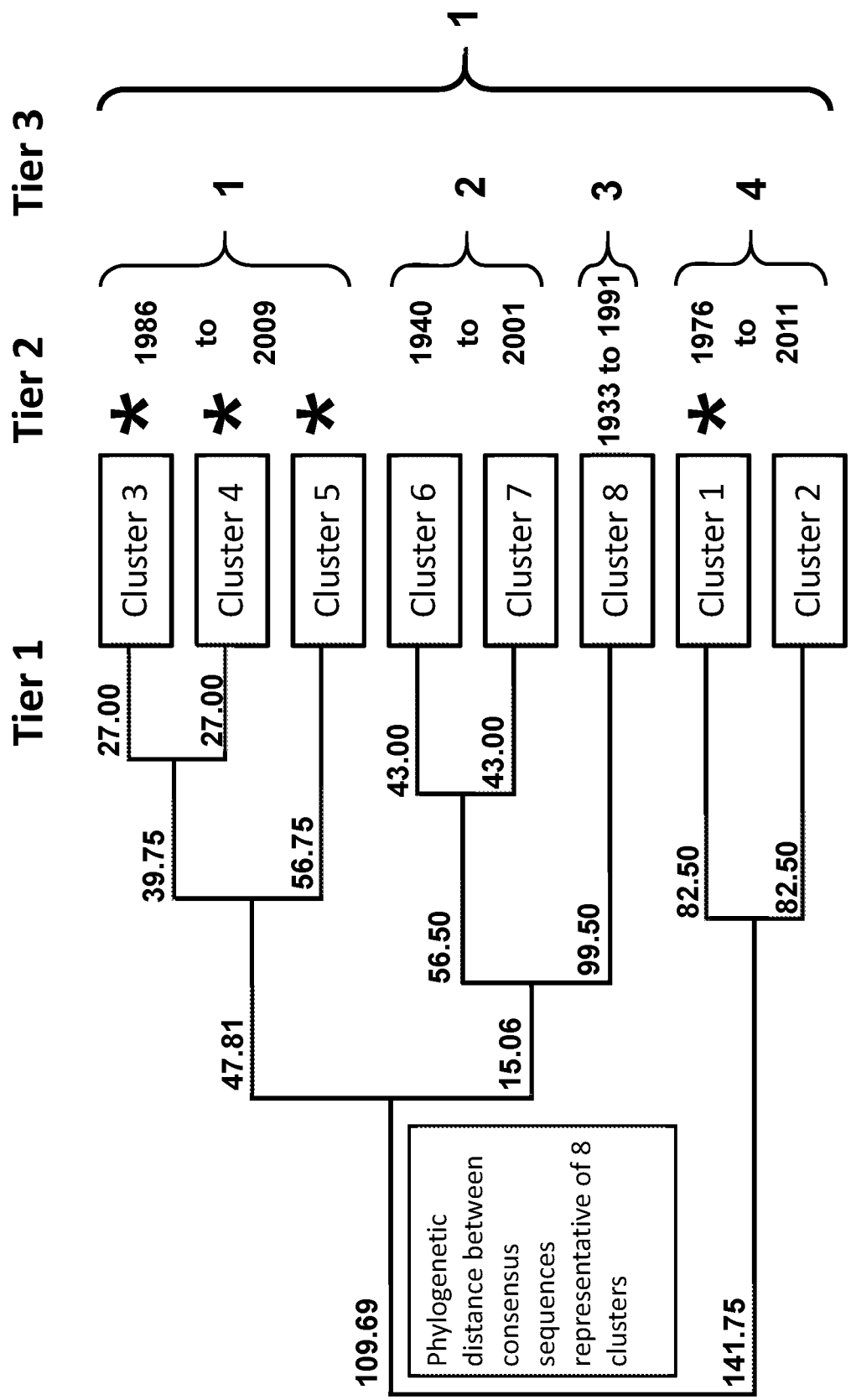

Example 1—Cluster-Based Consensus Approach for Designing Recombinant Influenza HA Polypeptides Recombinant influenza HA polypeptides were generated using a cluster-based consensus (CBC) approach. As a first step, influenza A hemagglutinin (HA) protein sequences (subtype H1N1) from 1918 through present (N=5664, of which 2043 were unique sequences) were downloaded from the Influenza Virus Resource at the National Center for Biotechnology Information (see Bao et al. (2008) J. Virol. 82, 596-601). The HA sequences were edited to remove signal peptide sequences and trans-membrane regions. A multiple sequence alignment of the non-redundant set of 2043 unique sequences was then generated. A complete pairwise identity matrix (2043×2043) was calculated and used as the input for Principal Components Analysis (PCA). The first two components from PCA were retained allowing for a compact representation of the high dimensional input matrix in 2-dimensional Euclidean space. Eight representative clusters of related sequences were identified as shown in FIG. 1A.

Subsequently, sequences within each of the individual clusters were analyzed to identify the most frequently occurring residues at each position and to yield a representative HA polypeptide comprising consensus amino acid sequences. By way of example, if the frequency of the amino acid at a given position was 50% or greater, that amino acid was designated a consensus amino acid, and if the frequency of the amino acid at a given position was less than 50%, that amino acid is designated as a variable amino acid. In cases of amino acid variation at specific positions in the alignment (e.g., where the maximum frequency was <0.5) the decision on the representative amino acid at the position was based on analysis of structural models of the consensus sequences generated by comparative modeling.

Specifically, in cases where a clear majority vote could not define a single amino acid at a specific position in the sequence, multiple consensus sequences (one for each possible amino acid based on the alignment) were generated. Positions that could not be determined unambiguously were coded as 'X', to be resolved by molecular modeling from a unique set of probable amino acids that could occur at any one specific position. Accordingly, an important aspect of the design was refinement by molecular modeling to resolve potential structural problems and select suitable amino acids at variable positions and select sequences based on low calculated energies. For example, the 3D structures of sequences generated by the consensus method were modeled using the Rosetta Molecular Modeling package (Leaver-Fay et al. (2011) *Meth. Enzymol.* 487:545-74). Molecules with negative total energy values were predicted to have a high probability of folding into stable and/or functional proteins while those with positive energy values were considered less likely to fold properly. Thus, where residue positions could not be assigned unambiguously using the consensus generation method, the amino acid resulting in a structure with the lowest, or near to lowest, calculated potential energy was selected since it was presumed to be more stable and therefore likely to be expressed and functional.

Using this process, a set of energy minimized designs including multiple candidate sequences was generated. Particularly, a single representative sequence for each of the eight clusters (within-cluster archetype sequences) was selected for further evaluation. These representative sequences were denoted as "Tier 1" sequences. Four of the Tier 1 sequences appeared to be novel and were not present in the public databases. The other four sequences were known to have appeared naturally (cluster 1: A/Korea/CJ04/2009; cluster 3: A/Pennsylvania/02/2008; cluster 4: A/Wellington/10/2005; and cluster 5: A/Memphis/06/1996). The four naturally occurring sequences were not known to have been used as vaccine antigens and therefore would have novel application within the scope of the present invention.

To further extend the breadth of antigen coverage, multiple Tier 1 consensus sequences were combined to yield across-cluster consensus sequences using the same procedure for defining a consensus sequence and structural modeling as described previously. Using this procedure, the combined grouping of Tier 1 archetype sequences resulted in three 'Tier 2' sequences. Specifically, the combination of clusters 1 and 2 yielded "pandemic or swine-like" Tier 2 sequences; the combination of clusters 3, 4, and 5 yielded "seasonal-like group 1" Tier 2 sequences; and the combination of clusters 6 and 7 yielded "seasonal-like group 2" Tier 2 sequences.

The process was repeated yet again by merging the Tier 2 sequences to calculate and subsequently generate "Tier 3" consensus sequences. Particularly, the Tier 2 and Tier 3 consensus sequences were designed to address the unequal number of sequences found in the different sequence clusters and to minimize any potential masking of signals of smaller clusters by larger clusters with more sequences. In addition, the Tier 2 and Tier 3 sequences were also subjected to structure-guided modeling and design in order to assess the stability of the sequences, resolve amino acid variation, and generate well-folded molecules exhibiting improved biophysical and immunological characteristics.

Exemplary Tier 1, Tier 2, and Tier 3 sequences designed using the cluster-based consensus approach described herein are presented in Table 1 as SEQ ID NOs: 1-16. These sequences are full-length HA sequences including signal peptides and transmembrane domains.

Example 2. In Vitro Expression of CBC HA Proteins

As the CBC HA proteins were designed according to criteria different from natural evolutionary processes, it was important to confirm correct expression, assembly, folding, and/or maintenance of epitope integrity. Accordingly, experiments were carried out to determine whether the Tier 1, Tier 2, and Tier 3 CBC HA proteins could be expressed on the surface of mammalian cells and be detected by anti-HA antibodies that recognized conserved epitopes in the head or stem region. In these experiments, antibody binding was assessed by flow cytometry.

Figure 2:
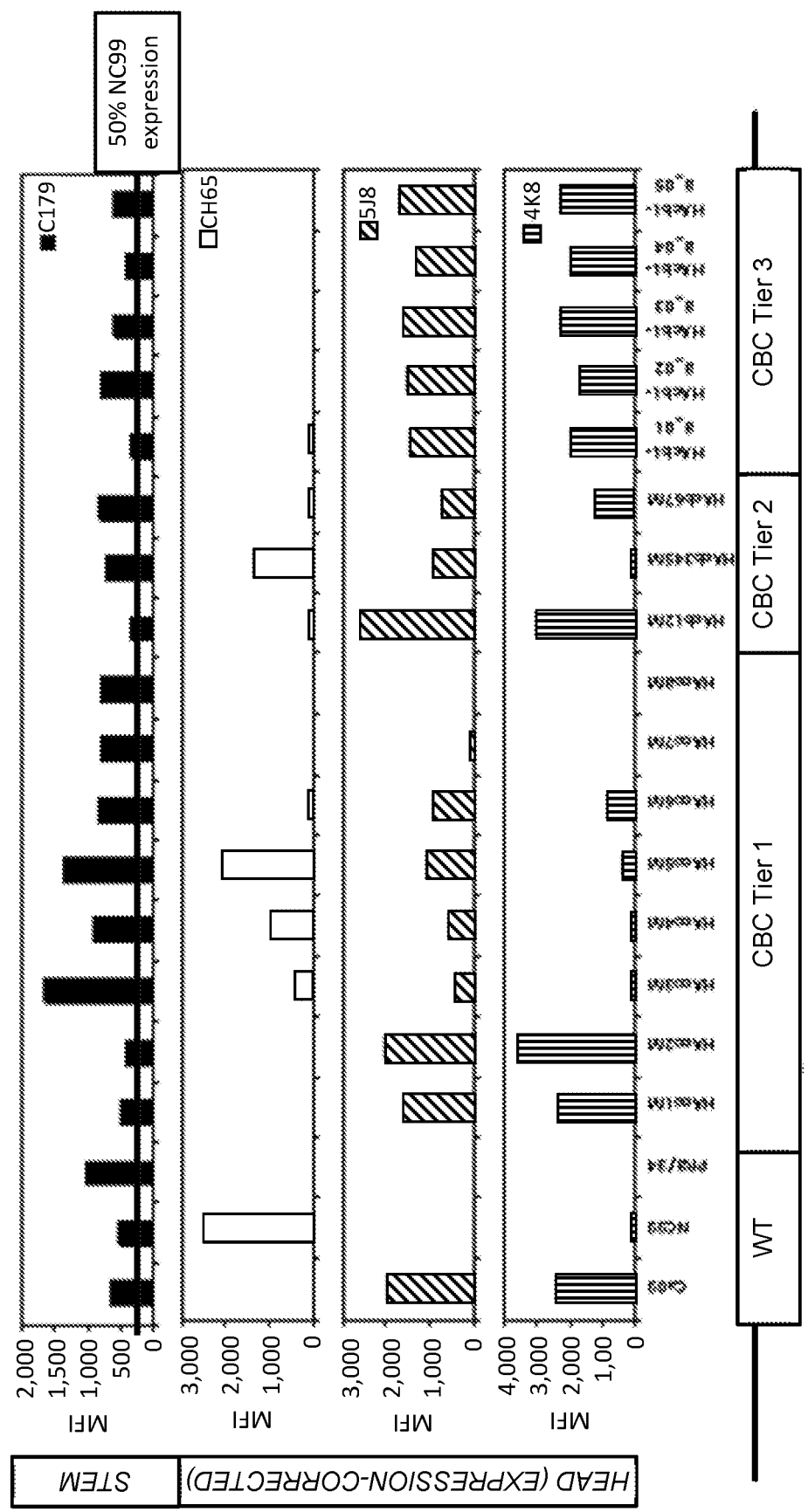
FIG. 2 illustrates that various Tier 1, Tier 2 and Tier 3 CBC HA polypeptides were properly folded and retained function. The CBC HA polypeptides were expressed in 293FT cells, and surface expression was detected using monoclonal antibodies that are known to recognize conserved epitopes in the globular head (i.e., CH65, 5J8, and 4K8) or stem (i.e., C179) regions.

For example, the monoclonal antibody C179 was known to bind conformational epitopes in the conserved HA stem domain of H1N1 HA proteins (Okuno, Y et al., J. Virology 1993). As shown in FIG. 2, the C179 antibody bound all of the wild type and CBC HA proteins tested although with varying efficiencies suggesting differences in epitope exposure or protein expression levels.

The three HA head-specific monoclonal antibodies (i.e., CH65, 5J8, and 4K8) recognized some, but not all, wild type and CBC HA proteins. Both 5J8 and 4K8 antibodies bound to the HA from A/California/07/2009 (Ca09), while failed to bind the HA from A/New Caledonia/20/1999 (NC99). The CH65 antibody bound to the HA of NC99, but did not bind to HA from pandemic Ca09. In comparison, both 5J8 and 4K8 antibodies bound to several Tier 1 and Tier 2 CBC HA proteins (i.e., HAco1M, HAco2M, HAco6M, HAcb12M, and HAcb67M), as well as all Tier 3 CBC HA proteins, suggesting that these CBC HA proteins may be antigenically related to Ca09. A distinct antibody binding pattern was displayed by the Tier 1 and Tier 2 proteins HAco3M, HAco4M, HAco5M, and HAcb345M with respect to CH65 and 5J8 antibody binding, which was not observed with wild-type HA.

Altogether, these data indicate that all the CBC HA proteins were expressed, processed, and trafficked to the cell surface where they were correctly folded and presented to allow antibody binding. Further, the CBC HA proteins were functional and bound to sialic acids on red blood cells. Accordingly, the cluster-based consensus approach described herein was capable of generating HA polypeptides and proteins that fold properly and retained functions.

Figure 3:
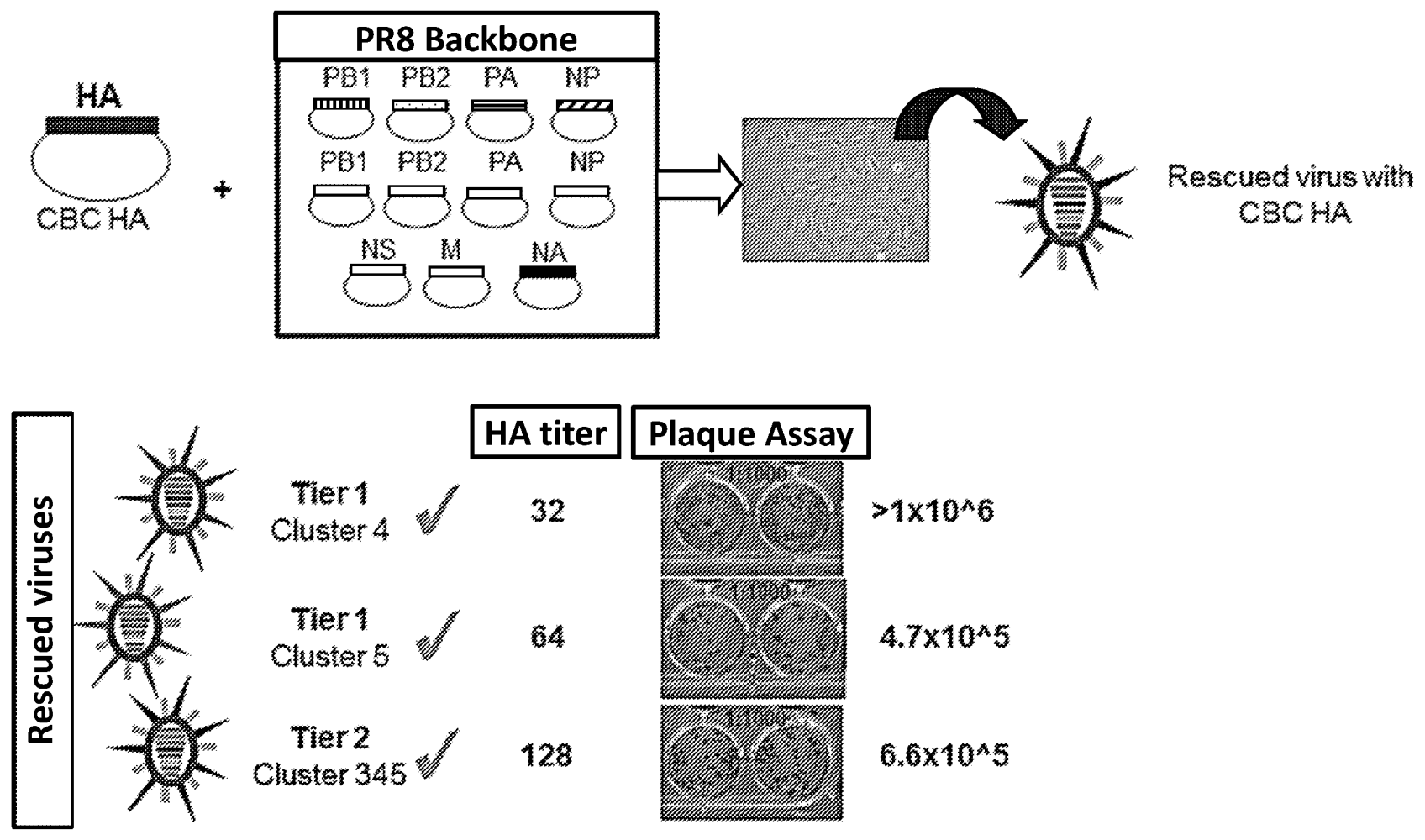

Example 3. Generation of Recombinant Influenza A Viruses Expressing CBC HA Sequences Influenza A viruses comprising CBC HA sequences were generated by reverse genetics. Specifically, a 12-plasmid reverse genetics system was used to generate recombinant A/Puerto Rico/8/1934 (PR8) H1N1 virus (an attenuated human virus that provided high-growth properties in eggs) that harbored a CBC HA sequence along with neuraminidase and eight other viral gene segments (FIG. 3). The 12 vectors were transfected into a mix of 293T and MDCK cells. After 3-4 days, cell culture supernatants were collected and inoculated into the allantoic cavities of embryonated chicken eggs for further viral propagation.

Successful rescue of influenza recombinant viruses harboring Tier 1 and 2 HA sequences (i.e., HAco3M, HAco4M, HAco5M, and HAcb345M) was demonstrated by detection of infectious viruses in plaque assay and determination of hemagglutinin activity (FIG. 3). The presence of the CBC HA sequences in recombinant viruses was also confirmed by Sanger sequencing.

These results demonstrated that influenza viruses expressing CBC HA sequences could be generated, and potentially made into split inactivated vaccines.

Example 4. Immunogenicity Studies of Recombinant Influenza A Viruses Expressing CBC HA Sequences The immunogenicity of recombinant influenza A viruses expressing CBC HA sequences was evaluated. FIG. 4 provides a schematic of the different immunogenicity studies.

Plaque reduction neutralization test (PRNT) was performed to assess the capacity of recombinant viruses to induce neutralizing antibodies against a panel of viruses. Particularly, the panel included viruses from multiple HA sequence clusters (see FIG. 5G). Mice were intranasally infected with recombinant viruses expressing various tier 1 and tier 2 CBC HA or wild type HA. Sera was collected from the infected mice and evaluated for induction of neutralizing antibodies.

Figure 5A:
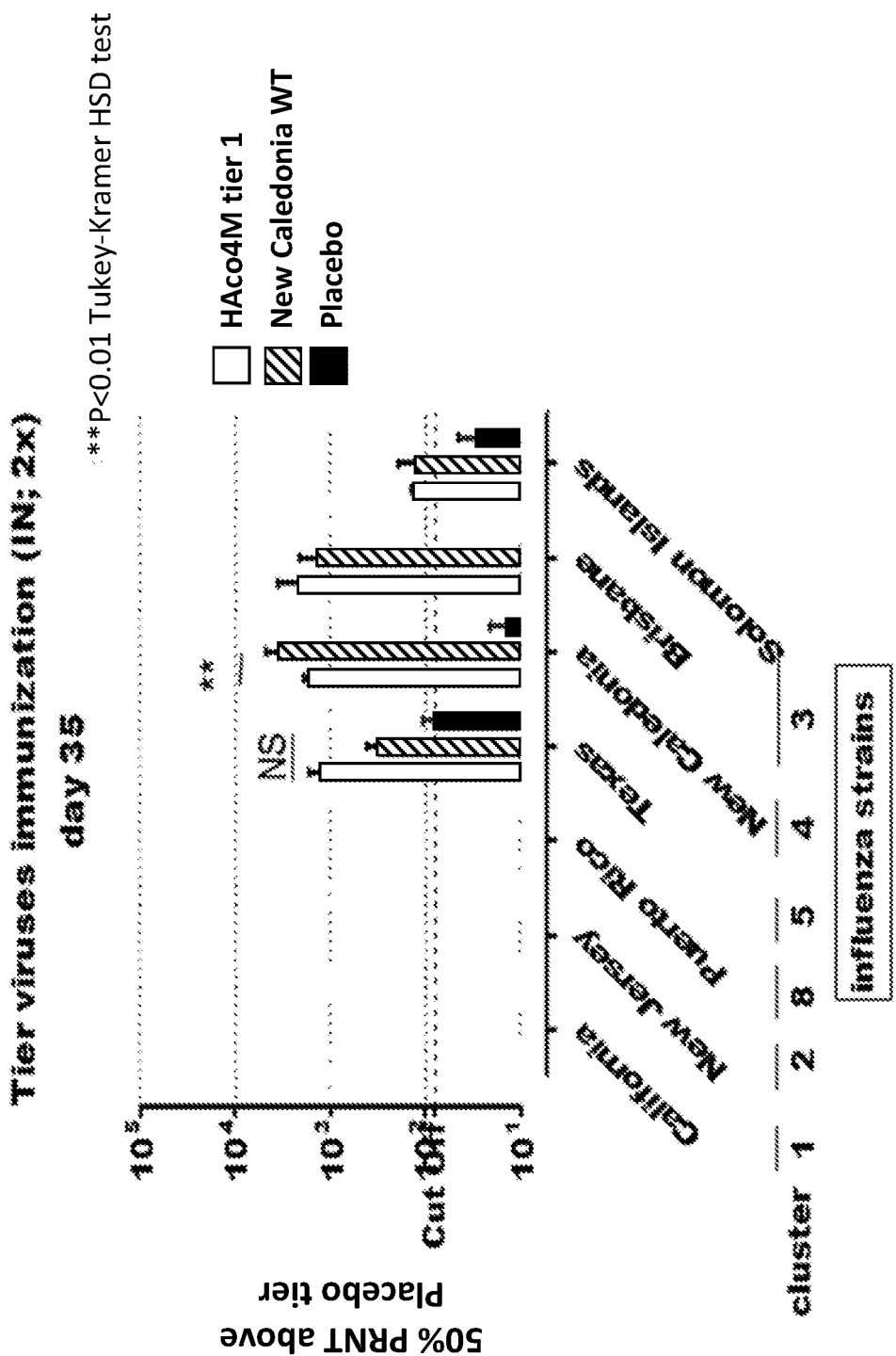
Figure 5B:
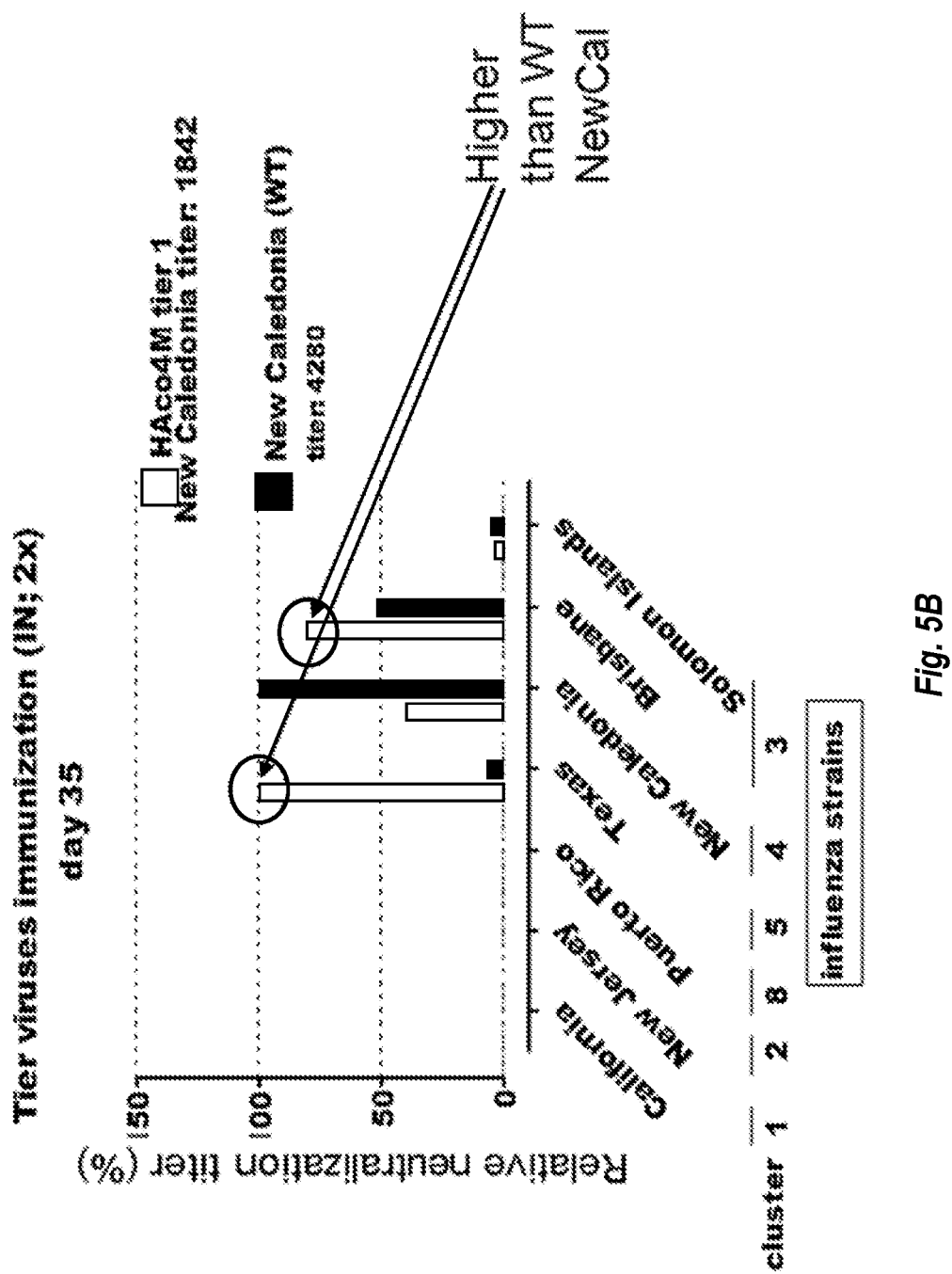

As shown in FIGS. 5A and 5B, recombinant virus expressing wild type A/New Caledonia/20/1999 HA (a virus from cluster 4) induced a fairly broad breadth of neutralization response against the panel of viruses. Recombinant virus expressing HAco4M (tier 1 CBC HA sequence derived from cluster 4) exhibited a breadth of protection comparable to virus expressing A/New Caledonia/20/1999 HA. Notably, the recombinant virus expressing HAco4M potentially induced an even higher neutralization response against the A/Texas/36/1991 virus (a virus from cluster 5) than the virus expressing wild type HA.

Figure 5C:
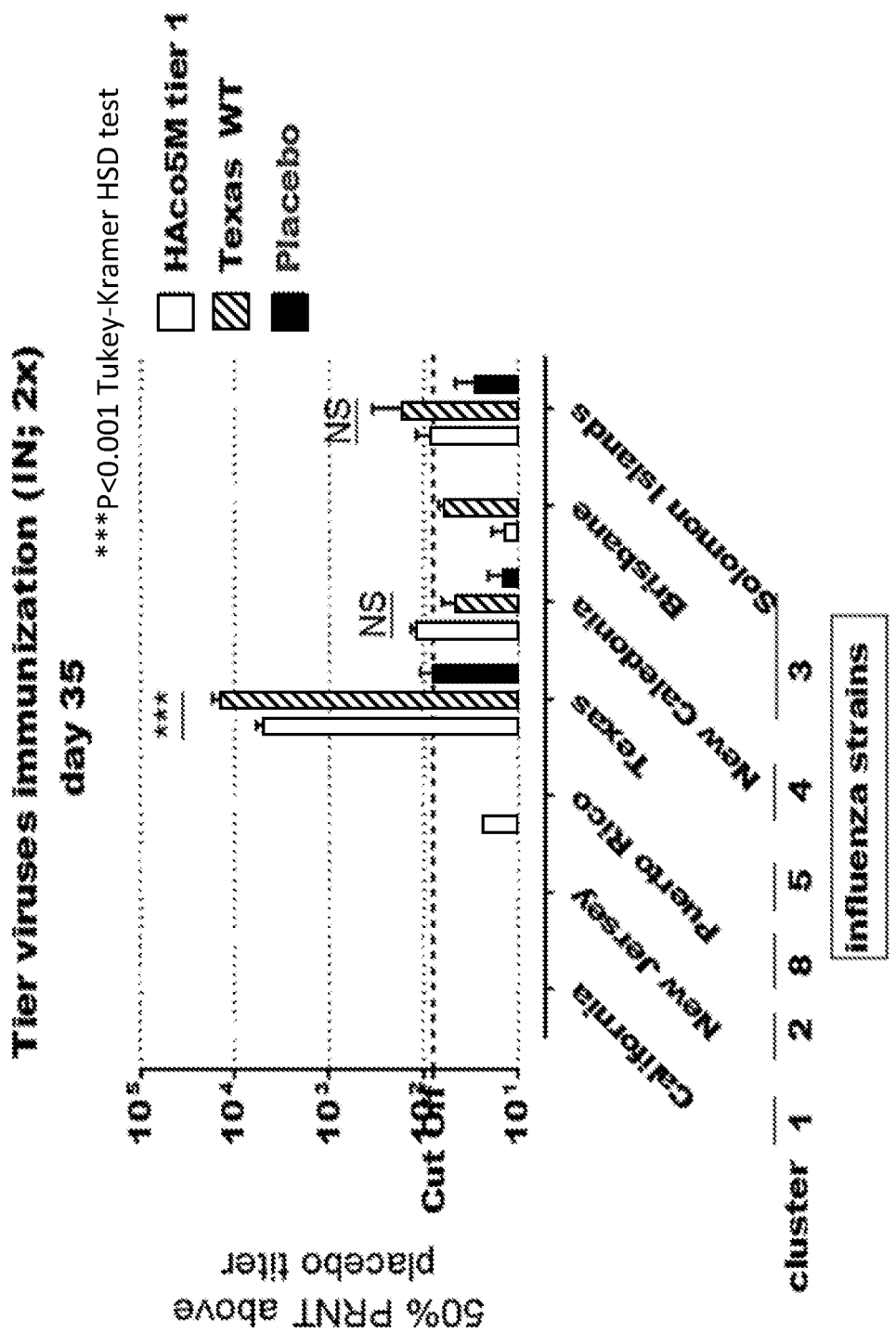

Recombinant virus expressing HAco5M (tier 1 CBC HA) was also evaluated, and its breadth of protection was compared to a recombinant virus expressing wild type A/Texas/36/1991 HA. As shown in FIG. 5C, the two recombinant viruses induced a similar breadth of neutralization response against the panel of viruses.

Figure 5D:
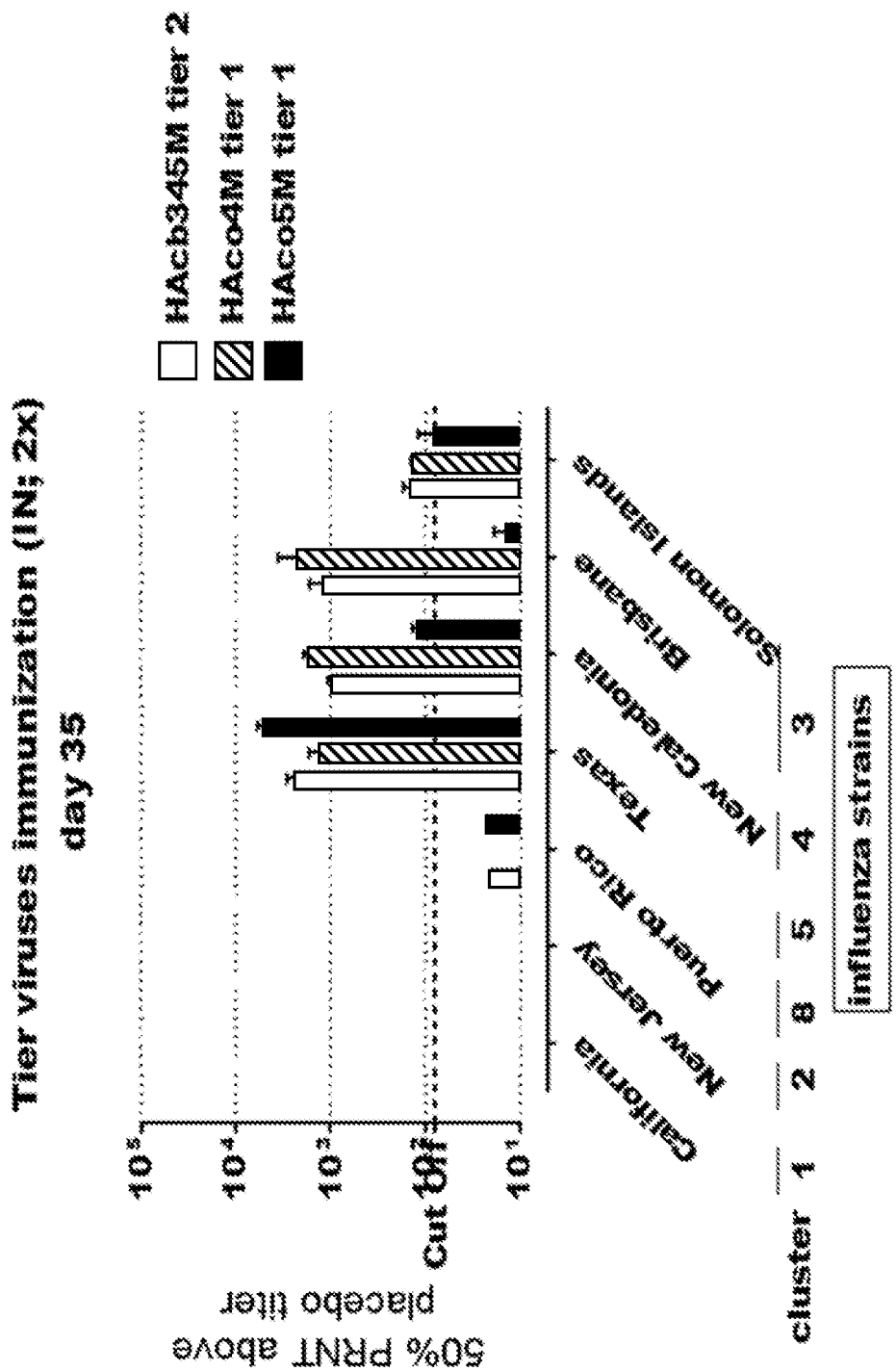

Additionally, the immunogenicity of recombinant virus expressing HAcb345M (a tier 2 CBC HA) was compared to recombinant viruses expressing tier 1 CBC HA (i.e., HAco4M and HAco5M). As shown in FIG. 5D, the recombinant virus expressing HAcb345M exhibited a similar neutralization response against the A/Brisbane/59/2007 virus (a cluster 3 virus) when compared to the virus expressing HAco4M. Notable, the recombinant virus expressing HAcb345M potentially exhibited a slightly improved activity against the cluster 4 A/Texas/36/1991 virus when compared to viruses expressing HAco4M and a significantly improved activity against cluster 3 A/Brisbane/59/2007 virus when compared to viruses expressing HAco5M (FIG. 5D).

Figure 5E:
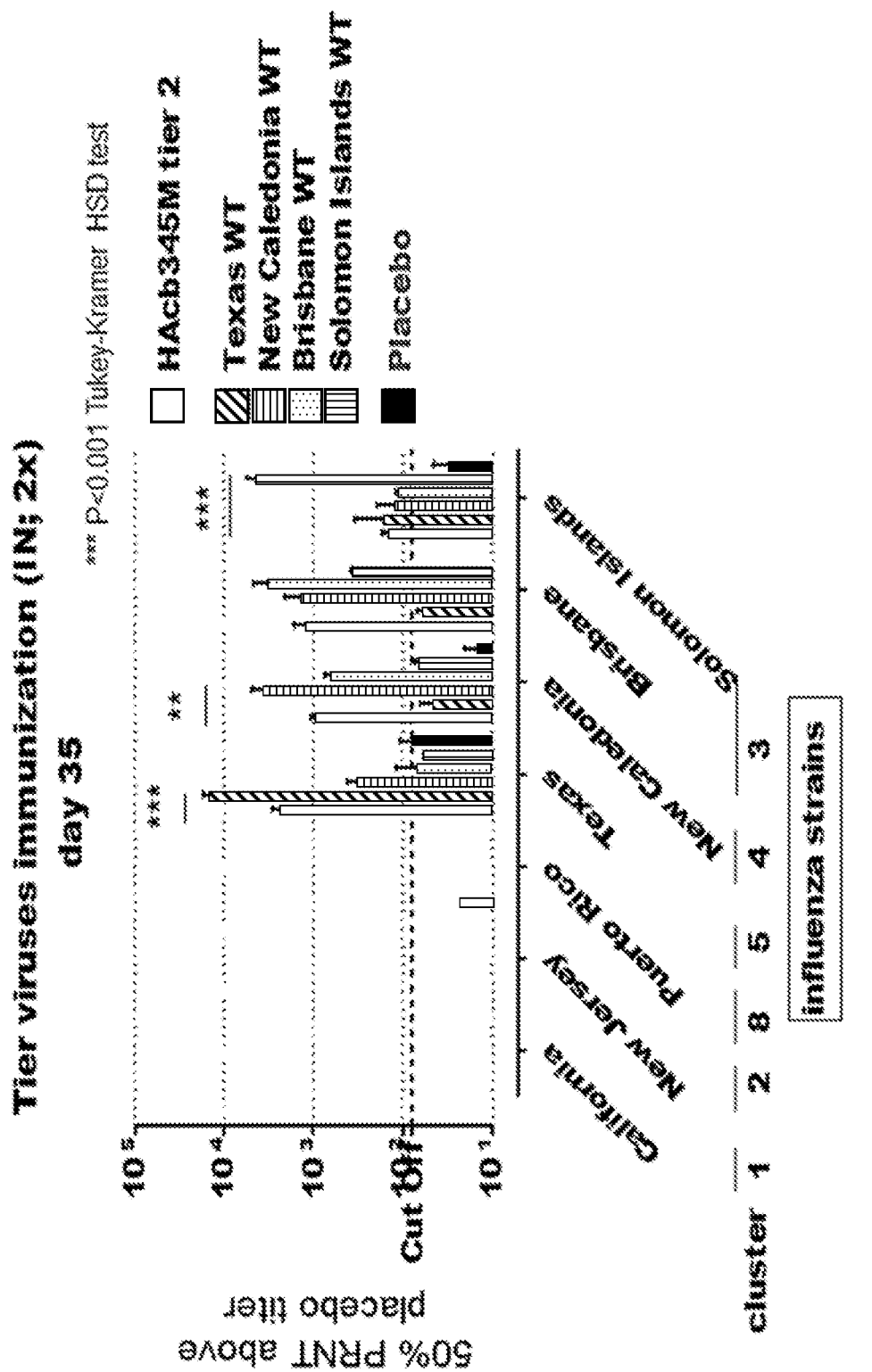
Figure 5F:
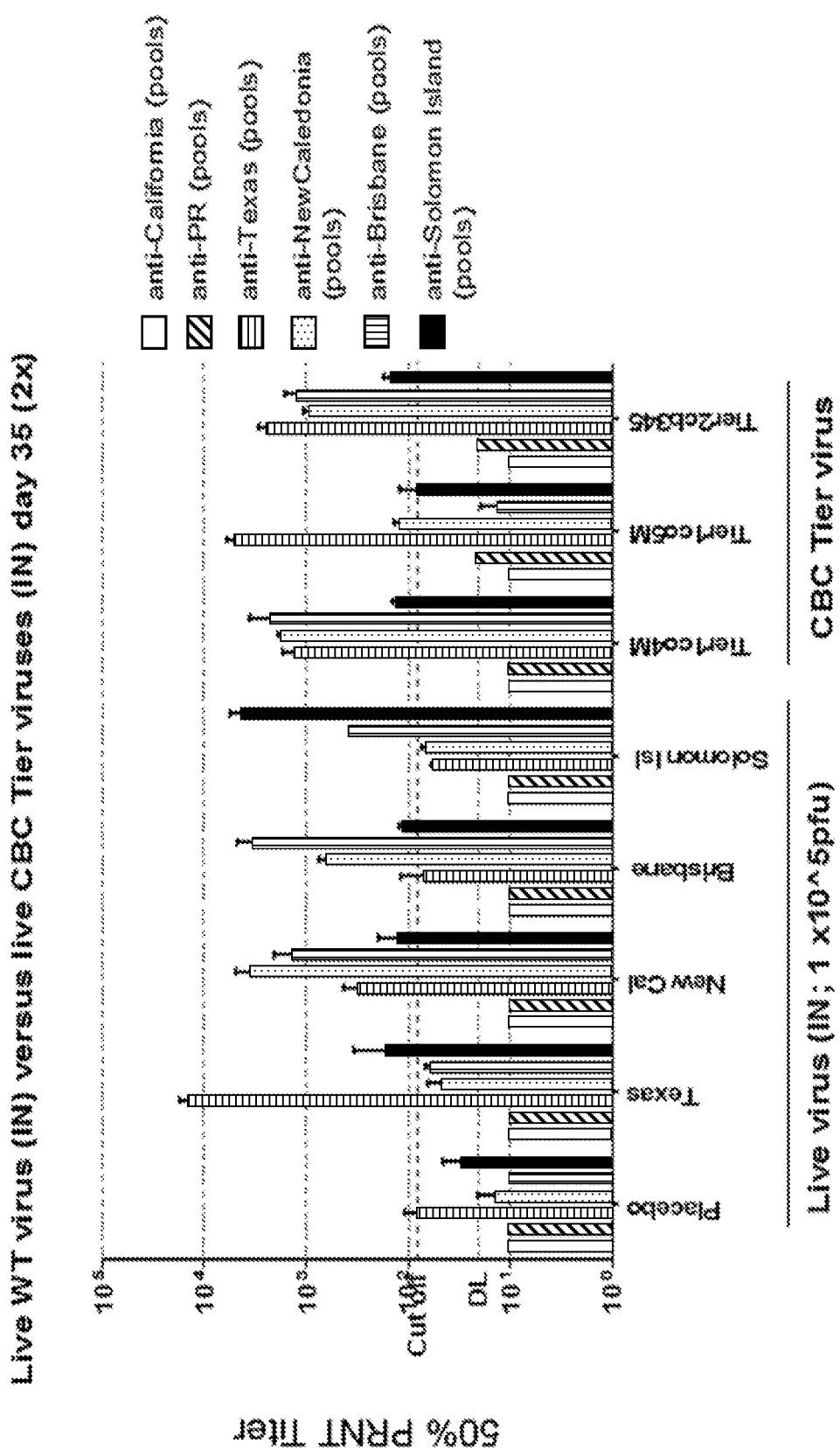
Figure 5G:
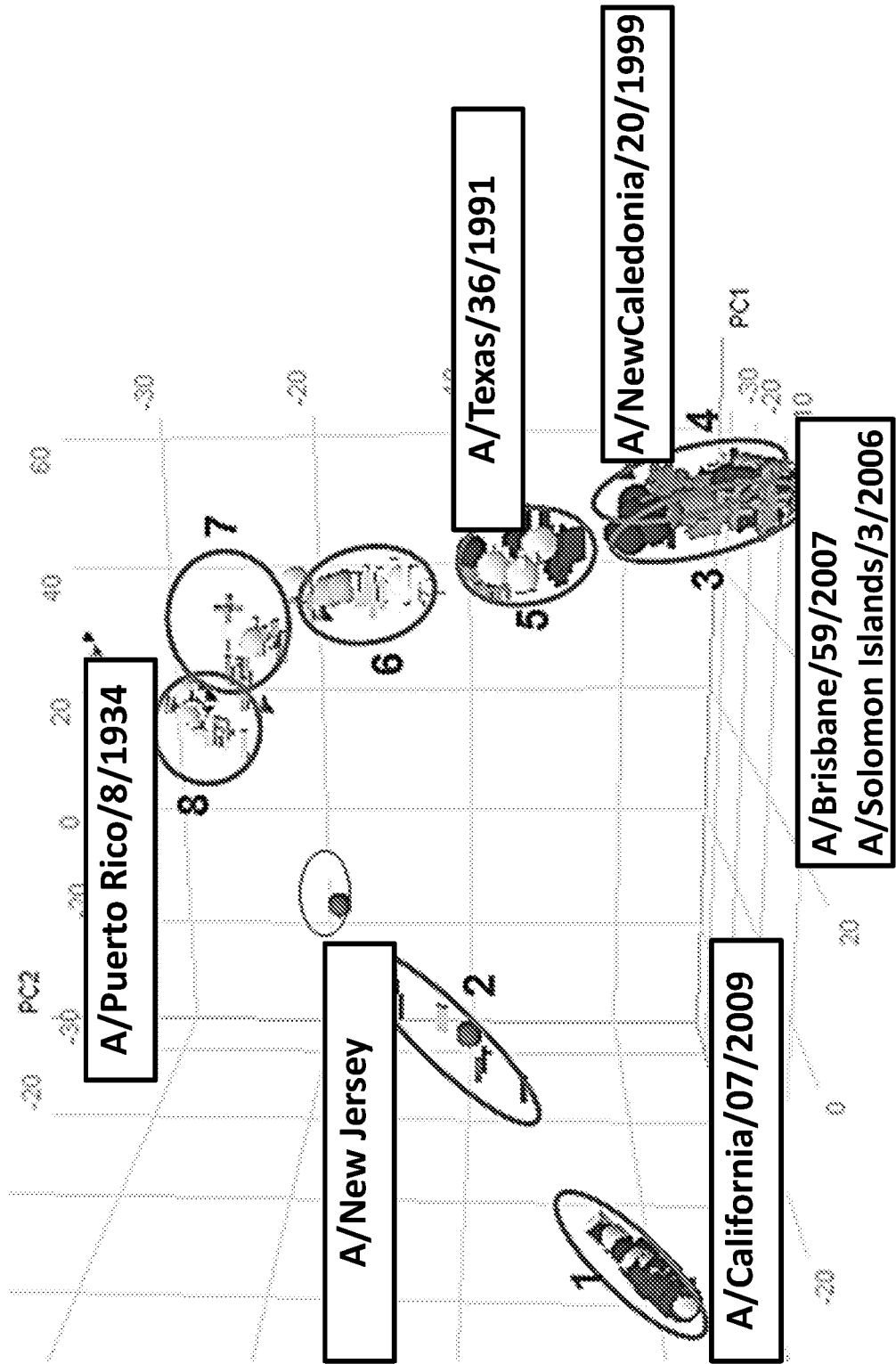

When compared to recombinant viruses expressing wild type HA, the recombinant virus expressing HAcb345M induced a comparable neutralization response against the A/Brisbane/59/2007 virus, but lower response against the A/Texas/36/1991, A/New Caledonia/20/1999, and A/Solomon Island/3/2006 viruses (FIG. 5E). Nevertheless, as shown in FIG. 5F, the recombinant virus expressing CBC HAcb345M exhibited a more balanced profile of neutralization against the panel of viruses tested, while wild type viruses exhibited strongest neutralizing antibody response against homologous viruses.

The immunogenicity of the various recombinant viruses was also evaluated by hemagglutinin inhibition (HAI) assays. The HAI assay protocol was adapted from the CDC laboratory-based influenza surveillance manual. As shown in FIG. 6, the HAI titers induced by recombinant viruses expressing CBC HA were comparable to those induced by recombinant viruses expressing wild type HA. Similar results were obtained when overall antibody binding was evaluated with the Antibody Forensics (AF) assay (FIGS. 7A-7D).

Example 6. Characterization of Virus-Like Particles (VLPs) Expressing CBC HA Proteins Immunization studies were performed to study the immunogenicity of virus-like particles (VLPs) expressing various CBC HA proteins. To generate the VLPs, HEK 293T cells were transiently transfected with plasmids expressing HIV-1 Gag, NA (A/mallard/Alberta/24/01; H7N3), and CBC HA or HA from wild type H1N1 strains, and incubated for 72 hours at 37° C. Supernatants were collected and cell debris removed by low speed centrifugation followed by vacuum filtration through a 0.22 μm sterile filter. VLPs were purified via ultracentrifugation (100,000×g through 20% glycerol, weight per volume) for 4 hours at 4° C. The pellets were subsequently resuspended in PBS pH 7.2 and stored in single use aliquots at −80C until use. Total protein concentration was determined by Micro BCA™ Protein Assay Reagent Kit (Pierce Biotechnology, Rockford, Ill., USA). The VLPs were characterized by electron microscopy as well as by dynamic light scattering analysis. Further, the amount of HA on the VLPs were quantitated by HA assays to show that the HA was functionally active.

For evaluation of the immunogenicity of the VLPs (in combination with the AF04 adjuvant), mice were subcutaneously injected twice on study days 0 and 21 (FIG. 8). For comparison, the mice were also challenged with a broad panel of representative live influenza viruses. Blood samples were then collected from the challenged mice on study days −1, 20, and 35. The serum samples were analyzed for influenza-specific antibody responses using hemagglutinin inhibition (HAI) and microneutralization (MN) assays.

As shown in FIG. 9, immunization with VLPs expressing wild type A/New Caledonia/20/1999 HA induced a similar breadth of neutralizing antibody response as live A/New Caledonia/20/1999 virus infection. However, VLP immunizations induced higher HAI titers. VLPs expressing CBC HAcb345M induced a fairly broad neutralizing antibody response as detected by both HAI assay (FIG. 9) and MN assay (FIG. 10). VLPs expressing CBC HAco5M also induced a reasonably broad and balanced neutralizing antibody response as detected in MN assays.

Altogether, these data demonstrate that exemplary HA proteins designed using the CBC approach were functional and capable of inducing neutralizing antibody response in vivo.

We claim:

1. A method for producing a recombinant influenza hemagglutinin (HA) polypeptide comprising consensus amino acids, wherein the method comprises:
   a. selecting more than one influenza HA polypeptide sequence and aligning the sequences;
   b. calculating pairwise similarity/dissimilarity matrices;
   c. identifying and creating clusters of similar sequences from the pairwise similarity/dissimilarity matrices;
   d. within each cluster, determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid;
   e. generating a first sequence comprising consensus amino acids and variable amino acids for each cluster;
   f. within the first sequence generated in step (e), determining a consensus amino acid for each variable amino acid position, by:
      i. generating a set of test sequences based on the first sequence, wherein test amino acids are placed at the variable amino acid positions;
      ii. performing molecular modeling for each of the test sequences;
      iii. determining a consensus amino acid for each variable amino acid position by selecting amino acid(s) that result in a polypeptide having a negative total energy value;
   g. producing the recombinant influenza HA polypeptide comprising the consensus amino acids; and
   h. isolating the produced recombinant influenza HA polypeptide.

2. The method of claim 1, wherein aligning the sequences comprises using MAFFT, MUSCLE, CLUSTAL OMEGA, FASTA, a combination thereof, or any other multiple sequence alignment software packages.

3. The method of claim 1, wherein calculating the pairwise similarity/dissimilarity matrices comprises using BLOSUM, PAM, IDENTITY substitution matrices, or a combination thereof.

4. The method of claim 1, wherein identifying and creating clusters of similar sequences from the pairwise similarity/dissimilarity matrices comprise using K-means clustering, minimax clustering, principle component analysis (PCA), multidimensional scaling (MDS), or a combination thereof.

5. The method of claim 1, wherein molecular modeling comprises comparing to a crystal structure of an influenza HA polypeptide or protein.

6. The method of claim 1, wherein molecular modeling comprises use of Rosetta or any other molecular modeling software.

7. The method of claim 1, wherein the test amino acids comprise any natural or non-natural amino acid found in proteins.

8. The method of claim 1, wherein further comprising after step (e) if a plurality of clusters is analyzed, comparing the first sequence generated in step (e) of a cluster with a first sequence generated in another cluster or multiple clusters by:

i. aligning the sequences generated in step (e) for each cluster;

ii. determining whether there is a consensus amino acid for each position in the sequence alignment using a pairwise alignment method, wherein if the frequency of the amino acid at a given position is 50% or greater, that amino acid is designated a consensus amino acid, and if the frequency of the amino acid at a given position is less than 50%, that amino acid is designated as a variable amino acid; and iii. generating a second sequence comprising consensus amino acids and variable amino acids, wherein the consensus amino acid is determined in step (f) within said second sequence generated.

9. The method of claim 8, wherein in step (f)(i) the set of test sequence is generated based on the second sequence.

* * * * *